US008822509B2

(12) United States Patent
Smith

(10) Patent No.: US 8,822,509 B2
(45) Date of Patent: Sep. 2, 2014

(54) PAIN-RELIEVING COMPOSITIONS AND USES THEREFOR

(75) Inventor: Maree Therese Smith, Bardon QLD (AU)

(73) Assignee: The University of Queensland, St. Lucia, Queensland (AU)

( * ) Notice: Subject to any disclaimer, the term of this patent is extended or adjusted under 35 U.S.C. 154(b) by 428 days.

(21) Appl. No.: 12/494,183

(22) Filed: Jun. 29, 2009

(65) Prior Publication Data

US 2009/0326017 A1 Dec. 31, 2009

Related U.S. Application Data

(63) Continuation-in-part of application No. PCT/AU2008/000003, filed on Jan. 2, 2008.

(30) Foreign Application Priority Data

| Dec. 29, 2006 | (AU) | ................................ | 2006907305 |
| Jul. 2, 2008 | (AU) | ................................ | 2008903394 |
| Aug. 15, 2008 | (AU) | ................................ | 2008904197 |
| Apr. 3, 2009 | (AU) | ................................ | 2009901445 |

(51) Int. Cl.
*A61K 31/00* (2006.01)
*A61K 31/21* (2006.01)
*C07D 271/08* (2006.01)
*A61K 31/4245* (2006.01)

(52) U.S. Cl.
CPC .............. *C07D 271/08* (2013.01); *A61K 31/21* (2013.01); *A61K 31/4245* (2013.01); *A61K 31/00* (2013.01)
USPC .......................................... 514/364; 548/125

(58) Field of Classification Search
None
See application file for complete search history.

(56) References Cited

U.S. PATENT DOCUMENTS

| 5,374,640 A | 12/1994 | Schönafinger et al. |
| 6,232,331 B1 | 5/2001 | Sankaranarayanan |
| 6,248,895 B1 | 6/2001 | Sankaranarayanan |
| 2006/0189603 A1 | 8/2006 | Garvey et al. |
| 2007/0202155 A1 | 8/2007 | Ang et al. |
| 2008/0114038 A1 | 5/2008 | Pedrazzoli et al. |

FOREIGN PATENT DOCUMENTS

| CA | 2149854 A1 | 11/1995 |
| EP | 0 683 159 A1 | 11/1995 |
| EP | 1690558 A1 | 8/2006 |
| WO | WO 98/58663 A1 | 12/1998 |
| WO | WO 02/05795 A2 | 1/2002 |
| WO | WO 02/17898 A2 | 3/2002 |
| WO | WO 03/078437 A1 | 9/2003 |
| WO | WO 2006/066362 A1 | 6/2006 |
| WO | 2007002764 A2 | 1/2007 |
| WO | WO 2007/016136 A2 | 2/2007 |
| WO | WO 2007/060112 A1 | 5/2007 |
| WO | WO 2007/100910 A2 | 9/2007 |

OTHER PUBLICATIONS

PDN treatment, http://www.pdn-info.co.uk/Treatments.html, 2010.*
Purakkatle, caplus an 2007:17773.*
Attal, N. 2000 "Chronic Neuropathic Pain: Mechanisms and Treatment " *Clinical Journal of Pain* 16(3$^{rd}$ Sup):S118-307.
Bertinaria, M. et al. 2003 "[3-(1H-Imidazol-4-yl)propyl]guanidines containing furoxan moieties: A new class of $H_3$-antagonists endowed with NO-donor properties" *Bioorganic & Medicinal Chemistry* 11:1197-1205.
Boschi, D. et al. 2006 "NO-donor phenols: a new class of products endowed with antioxidant and vasodilator properties" *J Med Chem* 49(10):2886-2897.
Boulton, A.J.M. 2003 "Treatment of symptomatic diabetic neuropathy" *Diabetes Metabolism Research and Reviews* 19:S16-S21.
Cameron, N.E. et al. 2001 "Vascular factors and metabolic interactions in the pathogenesis of diabetic neuropathy" *Diabetologia* 44(11):1973-88.
Cena, C. et al. 2006 "Use of the furoxan (1,2,5-oxadiazole 2-oxide) system in the design of new NO-donor antioxidant hybrids" *ARKIVOC* vii:301-309.
Chen, S.-R. et al. 2002 "Functional μ opioid receptors are reduced in the spinal cord dorsal horn of diabetic rats" *Anesthesiology* 97:1602-1608.
Corteix, C. et al. 1998 "Is the reduced efficacy of morphine in diabetic rats caused by alterations of opiate receptors or of morphine pharmacokinetics?" *J Pharmacol and Exp Therapeutics* 285:63-70.
Feldman, E.L. et al. 1999 "New insights into the pathogenesis of diabetic neuropathy" *Curr Opin Neurol* 12:553-63.
Fruttero, R. et al. 1989 "Unsymetrically substituted furoxanes. Part 11: Methylfuroxancarbaldehydes" *J Heterocyclic Chem* 26:1345-1347.
Fusman, R. et al. 2001 "Image analysis for the detection of increased erythrocyte, leukocyte and platelet adhesiveness/aggregation in the peripheral blood of patients with diabetes mellitus" *Acta Diabetol* 38:129-134.
Kamei, J. et al. 2001 "Therapeutic potential of PKC inhibitors in painful diabetic neuropathy" *Expert Opin Investig Drugs* 10:1653-1664.
McAuley, D.F. et al. 2000 "Vasoconstriction to endogenous endothelin-I is impaired in patients with Type II diabetes mellitus" *Clinical Science* 99:175-179.

(Continued)

*Primary Examiner* — Sun Jae Yoo
(74) *Attorney, Agent, or Firm* — Knobbe, Martens, Olson & Bear, LLP

(57) ABSTRACT

This invention discloses compositions and methods for inducing, promoting or otherwise facilitating pain relief. More particularly, the present invention discloses the use of sub-normovasodilatory doses of nitric oxide donors in the therapeutic management of vertebrate animals including humans, for the prevention or alleviation of pain, especially neuropathic pain. According to some embodiments of the present invention, nitric oxide donors are administered by any suitable route so as to provide concentrations of NO that are about ½ to $10^{-15}$ of those known to induce vasodilation in normal circulations.

17 Claims, 14 Drawing Sheets

(56) References Cited

OTHER PUBLICATIONS

Morley, G.K. et al. 1984 "Mechanism of pain in diabetic peripheral neuropathy" *The American J Medicine* 77:79-82.

Obrosova, I.G. et al. 2002 "An aldose reductase inhibitor reverses early diabetes-induced changes in peripheral nerve function, metabolism, and antioxidative defense" *FASEB Journal* 16:123-125.

Ohsawa, M. and Kamei, J. 1999 "Modification of the Expression of Naloxone-Precipitated Withdrawal Signs in Morphine-Dependent Mice by Diabetes: Possible Involvement of Protein Kinase C" *Jpn. J. Pharmacol* 79:303-311.

Sima, A.A.F and Sugimoto, K 1999 "Experimental diabetic neuropathy: an update" *Diabetologia* 42:773-788.

Wang, L. et al. 1996 "Relevance of phosphorylation state to opioid responsiveness in opiate naïve and tolerant/dependent tissue" *Brain Research* 723:61-69.

Lissin, L.W. 2001 "Maintaining the Endothelium: Preventive Strategies for Vessel Integrity" *Preventive Cardiology* 4:28-37.

Agrawal, R.P. et al. 2007 "Glyceryl Trinitrate Spray in the Management of Painful Diabetic Neuropathy: A Randomized Double Blind Placebo Controlled Cross-Over Study" *Diabetes Research & Clinical Practice* 77:161-167.

Yuen, K.C.J. et al. 2002 "Treatment of Chronic Painful Diabetic Neuropathy with Isosorbide Dinitrate Spray" *Diabetes Care* 25:1699-1703.

Klein, T. et al., Human surrogate models of neuropathic pain, Pain, 2005, vol. 115, pp. 227-233.

Kontinen, V.K. et al., Predictive validity of neuropathic pain models in pharmacological studies with a behavioral outcome in the rat: a systematic review, Proceedings of the 10th World Congress on Pain, Progress in Pain Research and Management, IASP Press, 2003, vol. 24, pp. 489-498.

McCleane, Gary, Pharmacological Management of Neuropathic Pain, Therapy in Practice, CNS Drugs, 2003, vol. 17, No. 14, pp. 1031-1043.

Wang, L.X. et al., Animal and cellular models of chronic pain, Advanced Drug Delivery Reviews, 2003, vol. 55, pp. 949-965.

Supplemental Search Report issued on May 15, 2012 for European Application No. EP 09 77 1836.

\* cited by examiner

PAIN-RELIEVING COMPOSITIONS AND USES THEREFOR

RELATED APPLICATIONS

This application is a Continuation in Part of International Application No.: PCT/AU2008/000003, filed Jan. 2, 2008, designating the U.S. and published in English on Jul. 10, 2008 as WO 2008/080194, which claims the benefit of Australian Application No. 2006907305, filed Dec. 29, 2006; and which claims the benefit of Australian Application No. 2008903394, filed Jul. 2, 2008; Australian Application No. 2008904197, filed Aug. 15, 2008 and Australian Application No. 2009901445, filed Apr. 3, 2009, all of which are incorporated by reference in their entireties.

FIELD OF THE INVENTION

This invention relates generally to compositions and methods for inducing, promoting or otherwise facilitating pain relief. More particularly, the present invention relates to the use of sub-normovasodilatory doses of nitric oxide donors in the therapeutic management of vertebrate animals including humans, for the prevention or alleviation of pain, especially neuropathic pain. According to some embodiments of the present invention, nitric oxide donors are administered by any suitable route so as to provide concentrations of NO that are about ½ to $10^{-15}$ of those known to induce vasodilation in normal circulations.

BACKGROUND OF THE INVENTION

Painful diabetic neuropathy (PDN) is a common and debilitating peripheral nerve complication of diabetes mellitus. By 1 year after the initial diagnosis of diabetes, 7% of patients report symptoms (e.g. pain, abnormal sensations) with the prevalence rising to 50% by 25 years of diabetes diagnosis (Sima and Sugimoto, *Diabetologia* 42: 773-788 1999; Cameron et al. *Diabetologia* 44: 1973-88 2001). Patients may present with one or more symptoms including burning sensations, lancinating and deep aching pains, depending upon the extent of nerve injury (Boulton, *Diabetes Metab Res Rev* 19: S16-21 2003). Numbness, tingling, and a sensation of tightness in the extremity are also commonly associated with PDN (Boulton, *Diabetes Metab Res Rev* 19: S16-21 2003). In addition, unpleasant abnormal sensations (dysaethesia), enhanced sensitivity to stimulation (hyperaesthesia), a heightened response to painful stimuli (hyperalgesia) and a distorted sense of touch producing allodynia (innocuous stimuli such as light brushstrokes of the skin produce pain) are all commonly reported by patients with diabetic neuropathy (Boulton, *Diabetes Metab Res Rev* 19: S16-21 2003).

There are no preventative treatments for PDN (Sima et al. *Diabetologica* 42: 773-788 1999), hence the therapeutic management of the condition is primarily palliative. This palliative management also represents a significant therapeutic obstacle, as the most efficient analgesic pharmaceuticals available, the μ-opioid receptor agonists such as morphine, are reportedly ineffective for the relief of PDN (Attal, *Clin J Pain* 16: S1118-30 2006). The mechanism underpinning the development of this opioid agonist hyposensitivity is unclear, but investigations have shown that poor glycaemic control can reduce pain tolerance and pain threshold and thus reduce the effectiveness of analgesics such as morphine (Morley et al. *Am J Med* 77(1): 79-83 1984). In addition, there may be diabetes-associated alterations in morphine pharmacokinetics (Courteix et al. *J Pharmacol Exp Ther* 285(1): 63-70 1998) and/or changes in opioid receptor function (Chen et al. *Anesthesiology* 97: 1602-1608 2002).

Although PDN is attributed primarily to poor glycaemic control over a prolonged period, the exact pathogenesis is poorly understood (Sima and Sugimoto, *Diabetologia* 42: 773-788 1999; Feldman et al. *Curr Opin Neurol* 12: 553-63 1999) Presently, there are two broad theories regarding the development of PDN: the vascular dysfunction theory and the metabolic dysfunction theory.

The vascular dysfunction theory proposes that changes in the blood supply to the nerves (the neurovasculature or vasa nervorum) occur secondary to haemodynamic abnormalities (such as accelerated platelet aggregation and increased blood viscosity) (Fusman et al *Acta Diabetol* 38(3): 129-34 2001). In addition, pathological changes in the small blood vessels of the neurovasculature may occur (such as reduction of the production of nitric oxide from the endothelial cells of blood vessels and acceleration of the reactivity on vasoconstrictive substances) (McAuley et al. *Clin Sci (Lond)* 99(3): 175-9 2000). These haemodynamic and vascular changes, acting independently or synergistically, are capable of causing the perineurial ischemia and subsequent endoneurial hypoxia observed in human patients and animal models of diabetes (Cameron et al. *Diabetologia* 44(11): 1973-88 2001). The end result of these abnormalities is nerve damage capable of causing the symptoms and signs of PDN.

On the other hand, in the metabolic dysfunction theory, the causes of nerve damage are mediated through the activation of the polyol metabolic pathway and through non-enzymatic protein glycation. These pathways induce mitochondrial and cytosolic $NAD^+/NADH$ redox imbalances and energy deficiencies in the nerves which can culminate in damage to neural and neurovascular tissues (Obrosova et al. *FASEB J* 16(1): 123-5 2002). In addition, these metabolic changes are thought to activate protein kinase C (PKC) which is capable of heightening pain responses (Kamei et al. *Expert Opin Investig Drugs* 10(9): 1653-64 2001) and also of producing μ-opioid agonist hyposensitivity (Wang et al. *Brain Res* 723 (1-2): 61-9 1996). Furthermore, heightened PKC activity is thought to reduce the binding affinity of μ-opioid receptors for ligands (Ohsawa et al. *Brain Res* 764:244-8 1998). The consequences of these metabolic abnormalities are nerve damage and the development of μ-opioid agonist hyposensitivity, as seen in patients with PDN.

It is likely that neither theory is mutually exclusive and proponents of both theories converge in the belief that, downstream of vascular dysfunction or metabolic abnormalities, there is an imbalance in the production of vaso-active compounds in the vasa nervorum which leads to hypoxic ischemia of diabetic nerves.

Of all the endogenous vasodilators, nitric oxide is the most potent and hence is a likely candidate for reduced synthesis and consequent diabetes-induced constrictions in vascular tone. As well as relaxing vascular smooth muscle, it also inhibits the processes of platelet aggregation, mitogenesis and proliferation of cultured vascular smooth muscle, and leucocyte adherence (Wroblewski et al *Prev Cardiol* 3(4): 172-177 2000). Nitric oxide is produced by the vascular endothelium by a group of enzymes called nitric oxide synthases. There are three isoforms of nitric oxide synthase (NOS) named according to their activity or the tissue type in which they were first described. These enzymes all convert the endogenous substrate, L-arginine, into L-citrulline, producing NO in the process.

Recent studies by the present inventors revealed unexpectedly that nitric oxide donors such as L-arginine can broadly prevent, attenuate and/or reverse the development of reduced analgesic sensitivity to an opioid receptor agonist such as morphine in neuropathic conditions, including peripheral neuropathic conditions such as PDN (see International Publication No. WO 2003/078437). This finding that nitric oxide donors can restore the analgesic sensitivity of opioid analgesics such as morphine in subjects with neuropathic conditions was significant because it allowed the use of these analgesics for treating or preventing pain in conditions, for which they were previously considered ineffective.

SUMMARY OF THE INVENTION

The present inventors have surprisingly discovered that nitric oxide (NO) donors which directly or indirectly generate NO at concentrations that are smaller than those known to induce vasodilation in normal circulations (also referred to herein as sub-normovasodilatory (SNV) concentrations), are effective in producing analgesia in subjects with a neuropathic condition without the need for co-administering opioid analgesics. Based on this discovery, the present inventors consider that specific embodiments of SNV concentrations can broadly range from about ½ to about $10^{-15}$ of those known to induce vasodilation in normal circulations.

Accordingly, one aspect of the present invention provides methods for the treatment or prophylaxis of a neuropathic condition in a subject. In some embodiments, the neuropathic condition is treated or prevented by administering to the subject at least one NO donor at a level that enhances NO and that does not alter normal systemic vascular tone in the subject. The NO donor may be administered without co-administration of an opioid analgesic. Thus, in these embodiments, the methods of treating or preventing the neuropathic condition consist essentially of administering the NO donor(s). Suitably, the level of NO is a sub-normovasodilatory (SNV) concentration that ranges from about ½ to about $10^{-15}$ of a reference concentration required to induce vasodilation in an anatomical site of a reference subject lacking a vascular condition, which suitably but not exclusively associates with the neuropathic condition to be treated or prevented. Illustrative anatomical sites include kidney, skin, skeletal muscle, arm, leg, tail and gastro-intestinal tract.

The NO donor is suitably administered in the form of a composition comprising a pharmaceutically acceptable carrier and/or diluent. The composition may be administered by injection, by topical application, or by the buccal, sublingual, rectal or oral routes, including sustained-release modes of administration, over a period of time and in amounts which are effective for delivering a SNV concentration of NO as broadly described above. In some embodiments, the NO donor is provided in a sustained release formulation (e.g., transdermal patch), which delivers a SNV concentration of NO as broadly described above. In some embodiments, the NO donor is a slow-release NO donor that delivers an SNV concentration of NO as broadly described above.

In accordance with the present invention, SNV concentrations of NO have been shown to prevent or attenuate the pain associated with a neuropathic condition. Thus, in another aspect, the invention provides methods for preventing or attenuating neuropathic pain, especially peripheral neuropathic pain, in a subject. In some embodiments, neuropathic pain is prevented or attenuated by administering to the subject at least one NO donor at a level that enhances NO and that does not alter normal systemic vascular tone in the subject, wherein the NO donor is suitably in the form of a composition comprising a pharmaceutically acceptable carrier and/or diluent.

In a further aspect, the present invention contemplates the use of a composition that consists essentially of at least one NO donor for producing analgesia in a subject, especially in a subject having a neuropathic condition, which is suitably a peripheral neuropathic condition such as PDN or a related condition, wherein the composition comprises at least one NO donor at a level that enhances NO and that does not alter normal systemic vascular tone in the subject. In some embodiments, the composition excludes an opioid analgesic or is used to produce analgesia in the absence of co-administering an opioid analgesic.

In a further aspect of the invention there is provided a compound of formula (I):

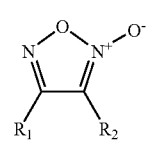

wherein $R_1$ and $R_2$ are independently selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylCO$_2$R$_3$, —$C_{0-6}$alkylC(O)R$_3$, —$C_{0-6}$alkylC(O)NHR$_4$, —$C_{0-6}$alkylN(R$_4$)$_2$, —$C_{0-6}$alkylN$^+$(R$_7$)$_3$, —$C_{0-6}$alkylOR$_5$, —$C_{0-6}$alkylSR$_5$, —$C_{0-6}$alkylC(=NR$_6$)R$_3$, —$C_{0-6}$alkylN=NR$_5$, —$C_{0-6}$alkylNR$_4$N(R$_4$,)$_2$, —$C_{0-6}$alkylNR$_4$C(=NR$_4$)N(R$_4$,)$_2$, —$C_{0-6}$alkylhalo, —$C_{0-6}$alkylS(O)R$_3$, —$C_{0-6}$alkylSO$_2$R$_3$, —CN and —NO$_2$; or $R_1$ and $R_2$ taken together form an optionally substituted 5 to 8 membered saturated or unsaturated carbocyclic or heterocyclic ring, an aryl ring or a heteroaryl ring;

$R_3$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{1-6}$alkylCO$_2$R$_7$, —$C_{0-6}$alkylN(R$_4$)$_2$, —$C_{1-6}$alkylNR$_4$C(=NR$_4$)N(R$_4$,)$_2$—$C_{1-6}$alkylOR$_7$ and —$C_{1-6}$alkylSR$_7$;

each $R_4$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylC(O)R$_8$, —$C_{0-6}$alkylC(S)R$_8$, —$C_{0-6}$alkylCO$_2$R$_7$, —$C_{0-6}$alkylSO$_2$R$_8$ and —$C_{0-6}$alkylOR$_7$;

$R_5$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylC(O)R$_7$, —$C_{0-6}$alkylCO$_2$R$_8$, —$C_{0-6}$alkylN(R$_7$)$_2$, —$C_{0-6}$alkylC(O)N(R$_7$)$_2$, —$C_{0-6}$alkylNR$_4$C(=NR$_4$)N(R$_4$,)$_2$, —$C_{1-6}$alkylOR$_7$ and —$C_{1-6}$alkylSR$_7$;

$R_6$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylNHC(O)N(R$_7$)$_2$, —$C_{0-6}$alkylNHC(O)R$_7$, —$C_{0-6}$alkylNHSO$_2$R$_7$, —$C_{0-6}$alkylNHCO$_2$R$_7$, —$C_{0-6}$alkylOC(O)R$_7$, —$C_{0-6}$alkylC(O)R$_7$, —CN and —OR$_7$;

each $R_7$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl and —$C_{0-6}$alkylheteroaryl; and $R_8$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl and —N(R$_7$)$_2$;

wherein each alkyl, alkenyl, alkynyl, cycloalkyl, cycloalkenyl, aryl, heterocyclyl and heteroaryl group is optionally substituted; or a pharmaceutically compatible salt thereof; wherein the compound is not 4-formyl-3-methyl-1,2,5-oxidiazole-2-oxide.

In a further aspect of the invention, there is provided a compound of formula (II):

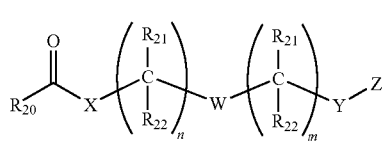

(II)

X is a covalent bond, —O—, —S— or —N($R_{23}$)—;
W is a covalent bond, —O—, —S—, —N($R_{23}$)— or —$C_6H_4$—;
Y is a covalent bond, —O— or —S—;
Z is —NO or —$NO_2$
$R_{20}$ is hydrogen, —OH, —Oalkyl, —$NH_2$, —NHalkyl or —N(alkyl)$_2$;
each $R_{21}$, and $R_{22}$ is independently selected from hydrogen, alkyl, alkenyl, alkynyl, cycloalkyl, halo, hydroxyl, alkyloxy, —$CO_2H$, —$CO_2$alkyl, —$CONH_2$, —CONHalkyl, —CON(alkyl)$_2$, aryl, heterocyclyl and heteroaryl;
$R_{23}$ is a hydrogen or alkyl;
n is 0 or an integer of 1-10; and
m is an integer of 1-10.

morphine (2.8 lμmol/Kg) and (C) vehicle, to groups of naïve (black circles) and "tolerant" (grey circles) non-diabetic rats.

Figure 14:
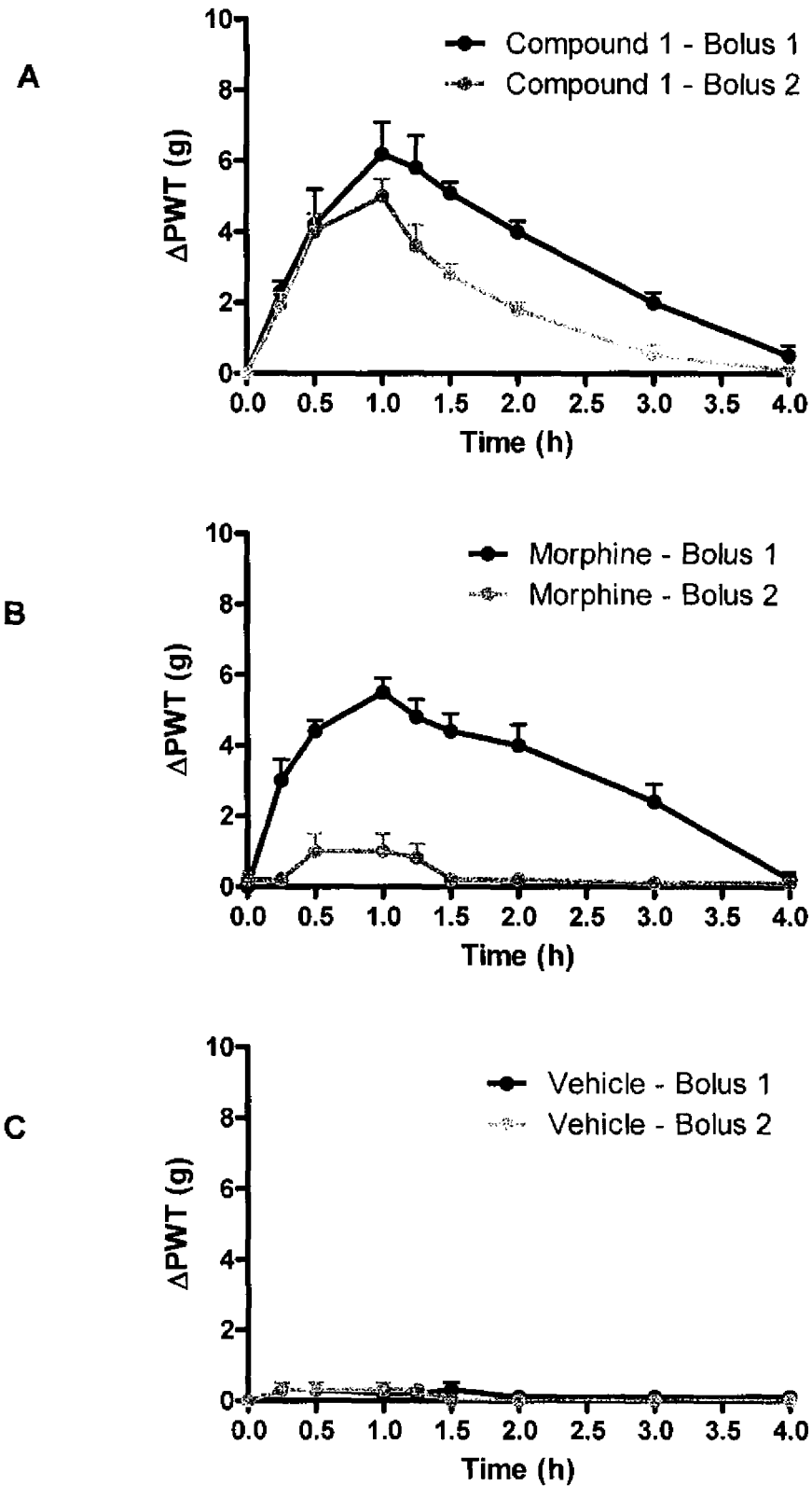

FIG. 14 is a graphical representation showing mean (±SEM) ΔPWT vs time curves following administration of single s.c. bolus doses of (A) Compound 1 (800 pmol/Kg), (B) morphine (2.8 μmol/Kg) and (C) vehicle, to groups of naive (black circles) and "tolerant" (grey circles) STZ-diabetic rats.

Figure 15:
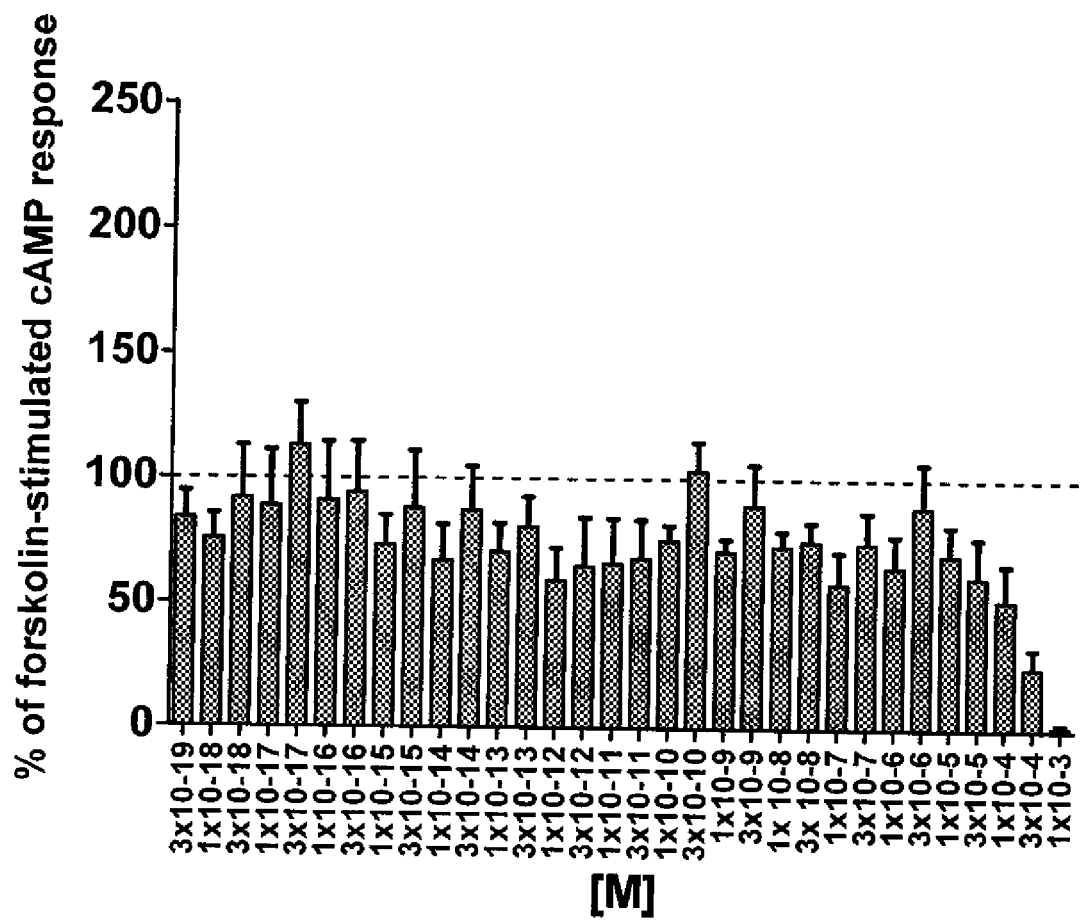

FIG. 15 is a graphical representation showing the effects of Compound 33 on forskolin-stimulated cAMP responses in mu-opioid receptor (MOP)-transfected HEK293 cells (Data are means±SEM., n=3).

Figure 16A:
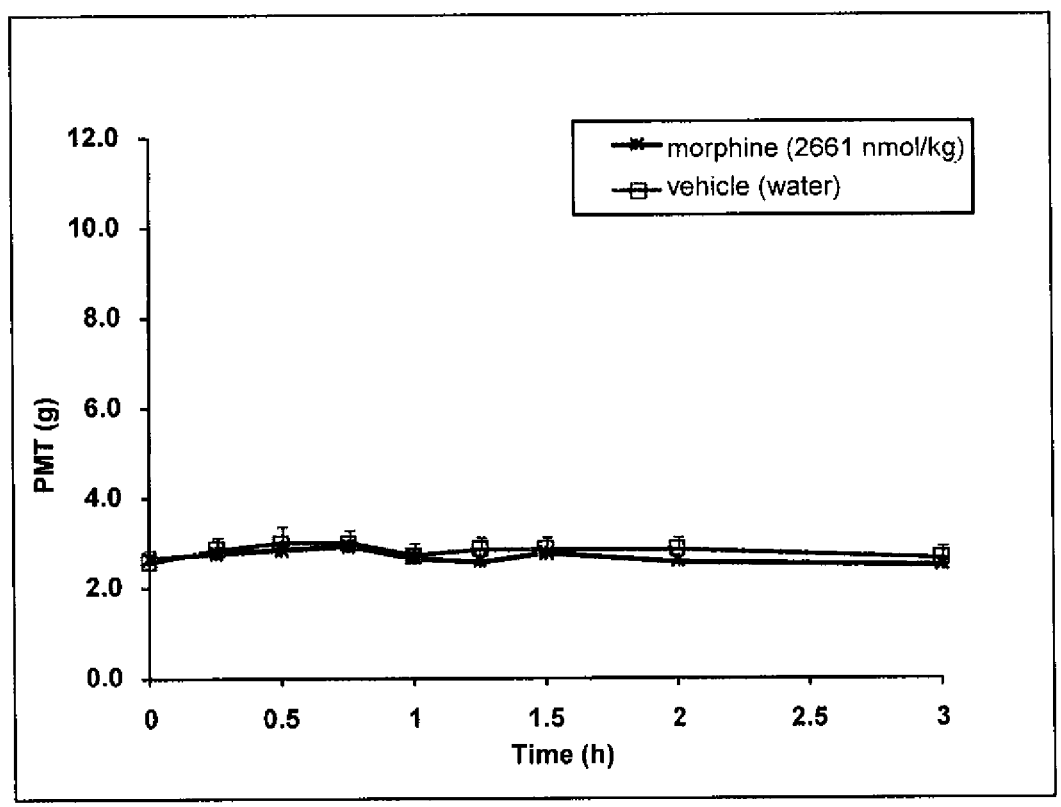

FIG. 16 is a graphical representation showing mean PWT vs time curves following administration of single s.c. bolus doses of (A) Morphine (2661 nmol/kg) and (B) compound 33 (80, 120, 800 and 1200 nmol/Kg).

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl, and decyl.

The term "alkenyl" as used herein refers to a straight chain or branched unsaturated hydrocarbon group having 2 to 10 carbon atoms and at least one double bond. Where appropriate, the alkenyl group may have a specified number of carbon atoms, for example, $C_{2-6}$ alkenyl which include alkenyl groups having 2, 3, 4, 5, or 6 carbon atoms in a linear or branched arrangement. Examples of suitable alkenyl groups include, but are not limited to, ethenyl, propenyl, 1-butenyl, 2-butenyl 1,3-butadienyl, 1-pentenyl, 2-pentenyl, 3-pentenyl, 4-pentenyl, 1,3-pentadienyl, 1,4-pentadienyl, 2,4-pentadienyl, 1-hexenyl, 2-hexenyl, 3-hexenyl, 4-hexenyl, 5-hexenyl, 1,3-hexadienyl, 1,4-hexadienyl, 1,5-hexadienyl, 2,4-hexadienyl, 1,3,5-hexatrienyl, heptenyl, octenyl, nonenyl and decenyl.

The term "alkynyl" as used herein refers to a straight chain or branched unsaturated hydrocarbon group having 2 to 10 carbon atoms and at least one triple bond. Where appropriate, the alkynyl group may have a specified number of carbon atoms, for example, $C_{2-6}$ alkynyl which includes alkynyl groups having 2, 3, 4, 5 or 6 carbon atoms in a linear or branched arrangement. Examples of suitable alkynyl groups include, but are not limited to, ethynyl, propynyl, butynyl, pentynyl, hexynyl, heptynyl, octynyl, nonynyl and decynyl.

The articles "a" and "an" are used herein to refer to one or to more than one (i.e. to at least one) of the grammatical object of the article. By way of example, "an element" means one element or more than one element.

As used herein, the term "about" refers to a quantity, level, concentration, value, dimension, size, or amount that varies by as much as 30%, 20%, or 10% or even as much as 9%, 8%, 7%, 6%, 5%, 4%, 3%, 2% or 1% to a reference quantity, level, concentration, value, dimension, size, or amount.

The term "allodynia" as used herein refers to pain that results from a non-noxious stimulus i.e., a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

As used herein, the term "aryl" is intended to mean any stable, monocyclic or bicyclic carbon ring of up to 7 atoms in each ring, wherein at least one ring is aromatic. Examples of such aryl groups include, but are not limited to, phenyl, naphthyl, tetrahydronaphthyl, indanyl, biphenyl and binaphthyl.

The term "causalgia" as used herein refers to the burning pain, allodynia and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. The phrases "consisting essentially of," "consists essentially of" and the like refer to the components which are essential in order to obtain the advantages of the present invention and any other components present would not significantly change the properties related to the inventive concept. Put another way, these phrases refer to the inclusion of any elements listed after the phrase, and limited to other elements that do not interfere with or contribute to the activity or action specified in the disclosure for the listed elements. Thus, the phrases "consisting essentially of," "consists essentially of" and the like indicate that the listed elements are required or mandatory, but that other elements are optional and may or may not be present depending upon whether or not they affect the activity or action of the listed elements.

The term "cycloalkyl" as used herein refers to a cyclic or caged saturated hydrocarbon ring having 3 to 8 carbon atoms. Examples of suitable cycloalkyl groups include, but are not limited to, cyclopropyl, cyclobutyl, cyclopentyl, cyclohexyl, cycloheptyl, cyclooctyl, norbornyl and adamantyl.

The term "cycloalkenyl" as used herein refers to a cyclic or caged unsaturated hydrocarbon ring having 3 to 8 carbon atoms and at least one double bond, but it is not aromatic. Examples of suitable cycloalkenyl groups include, but are not limited to, cyclopropentyl, cyclobutenyl, cyclopentenyl, cyclohexenyl, cyclohexadienyl, cycloheptenyl and cyclooctenyl.

By "effective amount", in the context of treating or preventing a condition (e.g. a neuropathic condition) is meant the administration of that amount of active to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the term "furoxan" denotes a 1,2,5-oxadiazole-2-oxide compound with a core structure:

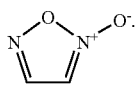

As used herein, the term "halogen" or "halo" refers to fluorine (fluoro), chlorine (chloro), bromine (bromo) and iodine (iodo).

The term "haloalkyl" as used herein refers to an alkyl group as defined above bearing one or more halo groups. Examples of haloalkyl groups include, but are not limited to, fluoromethyl, chloromethyl, bromomethyl, iodomethyl, difluoromethyl, dichloromethyl, fluorochloromethyl, trifluoromethyl, trichloromethyl, trifluoroethyl, trichloroethyl, pentafluoroethyl and pentachloroethyl.

The term "heterocyclic" or "heterocyclyl" as used herein, refers to a cyclic hydrocarbon in which one to four carbon atoms have been replaced by heteroatoms independently selected from N, S, O and Se. A heterocyclic ring may be saturated or unsaturated and/or may be fused to a carbocyclic, heterocyclic, aryl or heteroaryl ring. Examples of suitable heterocyclyl groups include, but are not limited to, tetrahydrofuranyl, tetrahydrothiophenyl, pyrrolidinyl, pyrrolinyl, pyranyl, piperidinyl, piperazinyl, pyrazolinyl, dithiolyl, oxathiolyl, dioxanyl, dioxinyl, morpholino, thiomorpholino, oxazinyl, azepinyl, diazepinyl, thiazepinyl, oxepinyl and thiapinyl and N-oxides thereof.

The term "heteroaryl" as used herein, represents a stable monocyclic or bicyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, pyrazolyl, indolyl, benzotriazolyl, furanyl, thienyl, thiophenyl, benzothienyl, benzofuranyl, quinolinyl, isoquinolinyl, oxazolyl, isoxazolyl, imidazolyl, pyrazinyl, pyridazinyl, pyridinyl, pyrimidinyl, pyrrolyl, tetrahydroquinoline, thiazolyl, isothiazolyl, 1,2,4-triazolyl, 1,2,4-oxadiazolyl, 1,2,4-thiadiazolyl, benzodioxanyl, benzazepinyl, benzoxepinyl, benzodiazepinyl, benzothiazepinyl and benzothiepinyl. Preferred heteroaryl groups have 5- or 6-membered rings, such as pyrazolyl, furanyl, thienyl, oxazolyl, isoxazolyl, imidazolyl, pyrazinyl, pyridazinyl, pyridinyl, pyrimidinyl, pyrrolyl, thiazolyl, isothiazolyl, 1,2,4-triazolyl and 1,2,4-oxadiazolyl and 1,2,4-thiadiazolyl and N-oxides thereof.

By "hyperalgesia" is meant an increased response to a stimulus that is normally painful.

As used herein, the term "low-release nitric oxide donor" or "low-release NO donor" is meant any substance that is converted or degraded or metabolized into, or provides an in vitro source of nitric oxide or NO to deliver a low concentration of nitric oxide into the blood stream. A low-release NO donor may provide rapid or immediate release of low levels of NO donor or may provide an initial rapid release of low levels of NO donor followed by an extended or graduated period of release of a low concentration of NO. The low-release NO donor may also be a slow-release NO donor. Suitably, the low-release NO donor is administered in an amount such that the NO is delivered into the blood stream in an amount of $10^{-2}$ to $10^{-15}$ of a reference concentration required to induce vasodilation in an anatomical site of a reference subject lacking vascular condition. A suitable amount of low-release NO donor delivered as a bolus amount is in the range of 0.000001 nmol/Kg to 2 nmol/Kg.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, painful diabetic neuropathy, post-herpetic neuralgia, phantom limb pain, sciatica, chemotherapy-induced neuropathy, HIV-AIDS-associated neuropathy, nerve entrapment pain, and the like.

By "nitric oxide donor," "NO donor" and the like is meant any substance that is converted into, degraded or metabolized into, or provides a source of in vivo nitric oxide or NO and includes any and all forms of NO which exist under physiological conditions. The, the term "NO donor" includes and encompasses any compound which mimics the effects of NO, generates or releases NO through biotransformation, any compound which generates NO spontaneously, any compound which spontaneously releases NO, or any compound which in any other manner generates NO or a NO-like moiety when administered to a subject.

"Nociceptive pain" refers to the normal, acute pain sensation evoked by activation of nociceptors located in non-damaged skin, viscera and other organs in the absence of sensitization.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28th Edition, W. B. Saunders Company, Philadelphia, Pa.). The goal of treatment of pain is to reduce the severity of pain perceived by a treatment subject.

By "pharmaceutically acceptable carrier" is meant a solid or liquid filler, diluent or encapsulating substance that may be safely used in topical, local or systemic administration.

The term "pharmaceutically compatible salt" as used herein refers to a salt which is toxicologically safe for human and animal administration. This salt may be selected from a group including hydrochlorides, hydrobromides, hydroiodides, sulphates, bisulphates, nitrates, citrates, tartrates, bitartrates, phosphates, malates, maleates, napsylates, fumarates, succinates, acetates, terephthalates, pamoates and pectinates.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The term "prodrug" is used in its broadest sense and encompasses those compounds that are converted in vivo to a NO donor according to the invention. Such compounds would readily occur to those of skill in the art, and include, for example, compounds where a free hydroxy group is converted into an ester derivative. Prodrug forms of compounds may be utilized, for example, to improve bioavailability, mask unpleasant characteristics such as bitter taste, alter solubility for intravenous use, or to provide site-specific delivery of the compound.

By "slow-release nitric oxide donor" or "slow-release NO donor" is meant any substance that is converted or degraded or metabolized into, or provides a source of in vivo nitric oxide or NO over an extended period of time, thereby delivering a low concentration of nitric oxide into the blood stream. Suitably the slow-release nitric oxide donor is administered in an amount such that nitric oxide is delivered at a rate of 0.000001 nmol/kg/hour to 2.0 nmol/kg/hour.

The terms "subject" or "individual" or "patient", used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment or prophylaxis for a peripheral neuropathic condition, especially PDN. However, it will be understood that the aforementioned terms do not imply that symptoms are present.

The term "sub-normovasodilatory concentration" or "SNC concentration" as used herein refers to a level of NO donor, which enhances NO and that does not alter normal systemic vascular tone in the subject.

The term "sustained-release formulation of nitric oxide donor" as used herein refers to a formulation of an NO donor that is adapted to release nitric oxide at a rate of 0.000001 nmol/kg/hour to 2.0 nmol/kg/hour or a range selected from 0.00001 nmol/kg/hour to 2.0 nmol/kg/hour, 0.0002 nmol/kg/hour to 1.0 nmol/kg/hour, 0.0005 nmol/kg/hour to 1.0 nmol/kg/hour, 0.0001 nmol/kg/hour to 0.5 nmol/kg/hour, 0.0002 nmol/kg/hour to 0.2 nmol/kg/hour, 0.0005 nmol/kg/hour to 0.1 nmol/kg/hour or 0.001 nmol/kg/hour to 0.05 nmol/kg/hour, 0.005 nmol/kg/hour to 0.01 nmol/kg/hour. The sustained release formulation may be any formulation capable of releasing NO at this rate. Illustrative sustained release formulations are transdermal patches adapted to deliver 0.1 nmol to 500 nmol per 24 hours, especially 10 nmol to 100 nmol per 24 hours, more especially 20 nmol to 60 nmol per 24 hours, most especially about 50 nmol over 6, 9, 12, 18, 24 or 30 hours.

By "does not alter normal systemic vascular tone" is meant not affecting mean arterial pressure so as to produce inappropriate systemic vasodilation with effects such as hypotension, headache, flushing in a normal subject or in a subject lacking a vascular condition (e.g., a neuropathic condition such as PDN).

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from $C_{1-6}$alkyl, $C_{2-6}$alkenyl, $C_{2-6}$alkynyl, $C_{3-6}$cycloalkyl, oxo (=O), $C_{1-6}$alkyloxy(CH$_2$)$_p$—, $C_{2-6}$alkenyloxy(CH$_2$)$_p$—, $C_{2-6}$alkynyloxy(CH$_2$)$_p$—, $C_{3-6}$cycloalkoxy(CH$_2$)$_p$—, $C_{1-6}$alkylthio(CH$_2$)$_p$—, $C_{2-6}$alkenylthio(CH$_2$)$_p$—, $C_{2-6}$alkynylthio(CH$_2$)$_p$—, $C_{3-6}$cycloalkylthio(CH$_2$)$_p$—, hydroxy(CH$_2$)$_p$—, —(CH$_2$)$_p$SH, —(CH$_2$)$_p$CO$_2$H, —(CH$_2$)$_p$CO$_2$C$_{1-6}$alkyl, —(CH$_2$)$_p$CON(R$_9$)$_2$, $C_{2-6}$acyl(CH$_2$)$_p$—, $C_{2-6}$acyloxy(CH$_2$)$_p$—, $C_{2-6}$alkylSO$_2$(CH$_2$)$_p$—, $C_{2-6}$alkenylSO$_2$(CH$_2$)$_p$—, $C_{2-6}$alkynylSO$_2$(CH$_2$)$_p$—, arylSO$_2$(CH$_2$)$_p$—, heteroarylSO$_2$(CH$_2$)$_p$—, heterocyclylSO$_2$(CH$_2$)$_p$—, —(CH$_2$)$_p$NH$_2$, —(CH$_2$)$_p$NH(C$_{1-6}$alkyl), —(CH$_2$)$_p$N(C$_{1-6}$alkyl)$_2$, —(CH$_2$)$_p$NH(phenyl), —(CH$_2$)$_p$N(phenyl)$_2$, —(CH$_2$)$_p$NH(acyl), —(CH$_2$)$_p$N(acyl)(phenyl), —(CH$_2$)$_p$NH—(CH$_2$)$_p$—S-aryl, —(CH$_2$)$_p$N=NHC(O)NH$_2$, —(CH$_2$)$_p$C(R$_{10}$)$_3$, —(CH$_2$)$_p$OC(R$_{10}$)$_3$, —(CH$_2$)$_p$SC(R$_{10}$)$_3$, —(CH$_2$)$_p$CN, —(CH$_2$)$_p$NO$_2$, —(CH$_2$)$_p$halogen, —(CH$_2$)$_p$heterocyclyl, heterocyclyloxy(CH$_2$)$_p$—, —(CH$_2$)$_p$heteroaryl, heteroaryloxy(CH$_2$)$_p$—, —(CH$_2$)$_p$aryl, —(CH$_2$)$_p$C(O)aryl and aryloxy(CH$_2$)$_p$— wherein each $R_{10}$ is independently selected from hydrogen and halogen; each $R_9$ is independently selected from H, $C_{1-6}$alkyl, phenyl, cycloalkyl or the two $R_9$ taken together with the nitrogen to which they are attached can form a heterocyclyl or heteroaryl ring; and p is 0 or an integer from 1 to 6. Examples of suitable substituents include, but are not limited to, methyl, ethyl, propyl, isopropyl, butyl, sec-butyl, tert-butyl, vinyl, oxo (=O), methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —CO$_2$H, —CO$_2$CH$_3$, —CO$_2$CH$_2$CH$_3$—CH$_2$CO$_2$CH$_3$, trifluoromethyl, trifluoromethoxy, trifluoromethylthio, acetyl, morpholino, amino, methylamino, dimethylamino, phenyl, phenylcarbonyl, NHCOphenyl, NHCObenzyl.

2. Methods for the Production of Analgesia and Compounds of the Invention

The present invention provides methods for producing analgesia in a subject having a neuropathic condition. These methods generally comprise administering to the subject at least one NO donor at a level that enhances NO and that does not alter normal systemic vascular tone in the subject. Suitably, this level equates to one that does not induce vasodilation, or not appreciably, in "healthy" or non-NO deficient circulations. Suitably, the level of NO is a sub-normovasodilatory (SNV) concentration that ranges from about ½ to about $10^{-15}$ of those currently used in clinical applications.

The method of the present invention has particular utility in the prevention and/or alleviation of the painful symptoms associated with neuropathic conditions. There are many possible causes of neuropathic conditions and it will be understood that the present invention contemplates the treatment and/or prevention of pain associated with any neuropathic condition regardless of the cause. In one embodiment, the neuropathic conditions are a result of diseases of the nerves (primary neuropathy) and neuropathy that is caused by systemic disease (secondary neuropathy), such as but not limited to diabetic neuropathy, Herpes Zoster (shingles)-related neuropathy, phantom limb pain, uraemia-associated neuropathy, amyloidosis neuropathy, HIV sensory neuropathies, hereditary motor and sensory neuropathies (HMSN), hereditary sensory neuropathies (HSNs), hereditary sensory and autonomic neuropathies, hereditary neuropathies with ulcero-mutilation, nitrofurantoin neuropathy, tomaculous neuropathy, neuropathy caused by nutritional deficiency and neuropathy caused by kidney failure. Other causes include repetitive activities such as typing or working on an assembly line, medications known to cause peripheral neuropathy such as several AIDS drugs (DDC and DDI), antibiotics (metronidazole, an antibiotic used for Crohn's disease, isoniazid used for tuberculosis), gold compounds (used for rheumatoid arthritis), some chemotherapy drugs (such as cisplatin, vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In another embodiment, the neuropathic condition is a peripheral neuropathic condition such as PDN or related condition.

The neuropathic condition may be acute or chronic and, in this connection, it will be understood by persons of skill in the art that the time course of a neuropathy will vary, based on its underlying cause. With trauma, the onset of symptoms may be acute, or sudden, with the most severe symptoms being present at the onset or developing subsequently. Inflammatory and some metabolic neuropathies have a subacute course extending over days to weeks. A chronic course over weeks to months usually indicates a toxic or metabolic neuropathy. A chronic, slowly progressive neuropathy over many years occurs with most hereditary neuropathies or with a condition termed chronic inflammatory demyelinating polyradiculoneuropathy (CIDP). Neuropathic conditions with symptoms that relapse and remit include the Guillian-Barre syndrome.

The NO donor includes and encompasses any substance that is converted into, or degraded or metabolized into, or provides a source of, in vivo NO, inclusive of NO in its various redox forms. The presence of nitric oxide (NO) in biological systems is usually inferred based on its physiological effect. However, several different redox forms of NO such as the NO free radical (NO.), the nitrosonium cation ($NO^+$), the nitroxyl anion ($NO^-$) or other oxides of nitrogen (NOx) are known to exist under physiological conditions and there is no clear evidence to suggest that one form is favored over another (Butler et al. 1995, Trends Pharmacol. Sci. 16:18-22; Stamler et al. 1992, Science 258:1898-1902). NO is also know to react with thiols to form S-nitrosothiols (RS—NO) and may represent a long-term storage form for NO. The category of NO donors includes compounds having differing structural features. For example, NO donors include, but are not limited to: metabolic precursors of NO such as L-arginine and L-citrulline; so-called "organonitrates" such as nitroglycerin (GTN), glyceryl trinitrate, isosorbide 5-mononitrate (ISMN), isosorbide dinitrate (ISDN), pentaerythritol tetranitrate (PETN), erythrityl tetranitrate (ETN), amino acid derivatives such as N-hydroxy-L-arginine (NOHA), $N^6$-(1-iminoethyl)lysine) (L-NIL), L-$N^5$-(1-iminoethyl)ornithine (LN-NIO), N-methyl-L-arginine (L-NMMA), and S-nitrosoglutathione (SNOG); other compounds which generate or release NO under physiologic conditions such as S,S-dinitrosodithiol (SSDD), [N-[2-(nitroxyethyl)]-3-pyridinecarboxamide (nicorandil), sodium nitroprusside (SNP), S-nitroso-N-acetylpenicillamine (SNAP), 3-morpholino-sydnonimine (SIN-1), molsidomine, DEA-NONOate (2-(N, N-diethylamino)-diazenolate-2-oxide), spermine NONOate (N-[4-[1-(3-aminopropyl)-2-hydroxy-2-nitrosohydrazino] butyl-1,3-propanediamine), and NO gas, or a functional equivalent thereof. The organic nitrates GTN, ISMN, ISDN, ETN, and PETN, as well as nicorandil are commercially available in pharmaceutical dosage forms. SIN-1, SNAP, S-thioglutathione, L-NMMA, L-NIL, L-NIO, spermine NONOate, and DEA-NONOate are commercially available from Biotium, Inc. 183 Shoreline Court, Richmond, Calif., USA. In other embodiments, the NO donor is suitably selected from [3-(1H-Imidazol-4-yl)propyl]guanidines-containing furoxan moieties, as for example, described in Bertinaria et al. (2003, Bioorganic & Medicinal Chemistry 11: 1197-1205), NO-donor phenols as described, for example, in Boschi et al. (2006, *J. Med. Chem.* 49: 2886-2897), pseudo-jujubogenin glycosides such as dammarane-type triterpenoid saponins (e.g., bacopasaponins) as well as their derivatives or analogues.

In one embodiment of the present invention, the at least one NO donor is a furoxan NO donor, particularly a furoxan compound of formula (I):

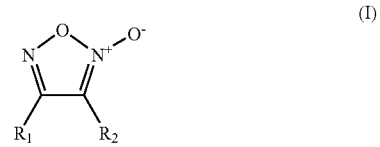

(I)

wherein $R_1$ and $R_2$ are independently selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkyl$CO_2R_3$, —$C_{0-6}$alkylC(O)$R_3$, —$C_{0-6}$alkylC(O)NH$R_4$, —$C_{0-6}$alkylN($R_4$)$_2$, —$C_{0-6}$alkyl$N^+$($R_7$)$_3$, —$C_{0-6}$alkylO$R_5$, —$C_{0-6}$alkylS$R_5$, —$C_{0-6}$alkylC(=N$R_6$)$R_3$, —$C_{0-6}$alkylN=N$R_5$, —$C_{0-6}$alkylN$R_4$N($R_4$)$_2$, —$C_{0-6}$alkylN$R_4$C(=N$R_4$)N($R_4$)$_2$, —$C_{0-6}$alkylhalo, —$C_{0-6}$alkylS(O)$R_3$, —$C_{0-6}$alkyl$SO_2R_3$, —CN and —$NO_2$; or $R_1$ and $R_2$ taken together form an optionally substituted 5 to 8 membered saturated or unsaturated carbocyclic or heterocyclic ring, an aryl ring or a heteroaryl ring;

$R_3$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{1-6}$alkyl$CO_2R_7$, —$C_{0-6}$alkylN($R_4$)$_2$, —$C_{1-6}$alkylN$R_4$C(=N$R_4$)N($R_4$)$_2$—$C_{1-6}$alkylO$R_7$ and —$C_{1-6}$alkylS$R_7$;

each $R_4$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylC(O)$R_8$, —$C_{0-6}$alkylC(S)$R_8$, —$C_{0-6}$alkyl$CO_2R_7$, —$C_{0-6}$alkyl$SO_2R_8$ and —$C_{0-6}$alkylO$R_7$;

$R_5$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylC(O)$R_7$, —$C_{0-6}$alkyl$CO_2R_8$, —$C_{0-6}$alkylN($R_7$)$_2$, —$C_{0-6}$alkylC(O)N($R_7$)$_2$, —$C_{0-6}$alkylN$R_4$C(=N$R_4$)N($R_4$)$_2$, —$C_{1-6}$alkylO$R_7$ and —$C_{1-6}$alkylS$R_7$;

$R_6$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylNHC(O)N($R_7$)$_2$, —$C_{0-6}$alkylNHC(O)$R_7$, —$C_{0-6}$alkylNHSO$_2R_7$, —$C_{0-6}$alkylNHCO$_2R_7$, —$C_{0-6}$alkylOC(O)$R_7$, —$C_{0-6}$alkylC(O)$R_7$, —CN and —O$R_7$;

each $R_7$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl and —$C_{0-6}$alkylheteroaryl; and $R_8$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl and —N($R_7$)$_2$;

wherein each alkyl, alkenyl, alkynyl, cycloalkyl, cycloalkenyl, aryl, heterocyclyl and heteroaryl group is optionally substituted; or a pharmaceutically compatible salt thereof.

In some embodiments, $R_1$ and $R_2$ are independently selected from —$C_{1-6}$alkyl, —$C_{3-8}$cycloalkyl, aryl, —COaryl, —C(O)H, —C(O)alkyl, —C(O)haloalkyl, —$NH_2$, —$NO_2$, —Salkyl, —Saryl, —$SO_2$alkyl, —$SO_2$aryl, —$CO_2$H, —$CO_2$alkyl, —$CO_2$haloalkyl, —$CO_2$aryl, —NHC(O)alkyl, —NHC(O)aryl, —N=NH, —N=Nalkyl, —N=Naryl, —C(=NOH)H, —OH, —Oalkyl, —Oaryl, —OC(O)alkyl, —OC(O)aryl, —OC(O)$NH_2$, —OC(O)NH(alkyl), —OC(O)N(alkyl)$_2$, —OC(O)N(alkyl)(aryl), —OC(O)N(aryl)$_2$, —OC(O)NH(aryl), —CH=NNHCO$_2$alkyl, —CH=NNHCO$_2$aryl, —CH=NNHC(O)NH$_2$, —CH=NNHC(O)NH(alkyl), —CH=NNHC(O)N(alkyl)$_2$, —CH=NNHC(O)NH(aryl), —CH=NNHC(O)N(alkyl)(aryl), —CH=NNHC(O)N(aryl)$_2$, —CH=NNHSO$_2$alkyl, —CH=NNHSO$_2$aryl, —CN, —CH$_2$OH, —C(O)NH$_2$, —C(O)NH(alkyl), —C(O)N(alkyl)$_2$, —C(O)NH(aryl), —C(O)N(alkyl)(aryl), —C(O)N(aryl)$_2$, —OalkylNH$_2$, —OalkylNH(alkyl), —OalkylN(alkyl)$_2$, —OalkylNHaryl, —OalkylN(aryl)$_2$, —OalkylN(aryl)(alkyl), —SalkylNH$_2$, —SalkylNH(alkyl), —SalkylN(alkyl)$_2$, —SalkylNHaryl, —SalkylN(aryl)$_2$, —SalkylN(aryl)(alkyl), —CH$_2$NH$_2$, —CH$_2$NH(alkyl), —CH$_2$N(alkyl)$_2$, —CH$_2$NH(aryl), —CH$_2$N(alkyl)(aryl), —CH$_2$N(aryl)$_2$, —C(O)heterocyclyl, —C(O)heteroaryl, —C(O)heterocyclyl-heteroaryl, —C(O)heteroaryl-heterocyclyl, —C(O)heterocyclyl-heterocyclyl, —C(O)heteroaryl-heteroaryl, —OalkylNHalkylOaryl, —OalkylNHC(O)heteroaryl and —OalkylOC(O)aryl, wherein each alkyl, aryl, heterocyclyl and heteroaryl is optionally substituted, or where $R_1$ and $R_2$ taken together with the carbon atoms to which they are attached form an optionally substituted 5 or 6 membered carbocyclic, aryl, heterocyclic or heteroaryl ring.

In some embodiments, $R_1$ and $R_2$ are independently selected from methyl, ethyl, propyl, isopropyl, cyclopentyl, cyclohexyl, phenyl, 4-fluorophenyl, 4-methoxyphenyl, 4-CH$_3$SO$_2$phenyl-, 4-NH$_2$SO$_2$phenyl-, 4-CH$_3$Sphenyl, phenylSO$_2$—, phenylS—, —NO$_2$, —NH$_2$, —C(O)H, —C(O)CH$_3$, —C(O)CF$_3$, —C(O)phenyl, —C(O)-4-fluorophenyl, —C(O)-4-chlorophenyl, —C(O)-2-chlorophenyl, —C(O)-2-methylphenyl, —C(O)-4-methylphenyl, —C(O)-2-methoxyphenyl, —C(O)-4-methoxyphenyl, —C(O)-4-cyanophenyl, —C(O)-3-cyanophenyl, —CO$_2$H, —NHC(O)CH$_3$, —N=N—H, —C(=NOH)H, —OH, —CH=NNHC(O)NHbutyl, —CH=NNHSO$_2$phenyl, —CH=NNHC(O)NHaryl, —CN, —OC(O)N(CH$_3$)(propyl), —CH$_2$OH, —C(O)NH$_2$, —OCH$_2$CH$_2$N(CH$_3$)$_2$, —SCH$_2$CH$_2$NH$_2$, —SCH$_2$CH$_2$N(CH$_3$)$_2$, —Omethyl, Oethyl, —CH$_2$N(CH$_3$)$_2$, —NHpropylOphenylCH$_2$—N-piperidine, —C(O)-1-piperidine-4-[2-(4-amino-6,7-dimethoxy-quinazoline)], —OpropylNH-(2-hydroxypropyl)oxynaphthalene, —Opropyl-NHC(O)-3-pyridine and O-alkylOC(O)-(2-acetylphenyl), or $R_1$ and $R_2$ taken together with the carbon atoms to which they are attached form a cyclopentyl ring, 2-oxo-cyclopentyl ring, cyclohexyl ring, 2-oxo-cyclohexyl ring, phenyl ring, 3-fluorophenyl ring, 3-methoxy-phenyl ring, 2N-pyridine ring or 3-N-pyridine ring.

In some embodiments, $R_1$ is not —C(O)H, especially when $R_2$ is methyl.

In some embodiments, the furoxan compound of formula (I) is 4-formyl-3-methyl-1,2,5-oxadiazole-2-oxide (Compound 1).

In some embodiments, $R_1$ and/or $R_2$ include a carbonyl or hydroxyl substituent, such as —$C_{0-6}$alkylCO$_2$R$_3$, —$C_{0-6}$alkylC(O)R$_3$, —$C_{0-6}$alkylC(O)NHR$_4$, —$C_{0-6}$alkylC(O)N(R$_4$)$_2$, —$C_{0-6}$alkylOH where $R_3$ and $R_4$ are as defined in formula (I) or where $R_1$ and $R_2$ taken together form a 5-8 membered saturated or unsaturated carbocyclic or heterocyclic ring substituted with an oxo (=O) group, especially where $R_1$ or $R_2$ are —CO$_2$H, —C(O)H, —C(O)NH$_2$, —C(O)CH$_3$, —C(O)CF$_3$, —CH$_2$OH, or where $R_1$ and $R_2$ taken together form a 5 or 6 membered carboxyclic ring substituted with an oxo (=O) group.

In some embodiments $R_1$ and/or $R_2$ include an optionally substituted phenyl ring, especially an unsubstituted phenyl ring or a phenyl ring substituted with at least one substituent selected from alkyl, hydroxy, alkoxy, halo and cyano, especially alkoxy and halo, more especially methoxy and fluoro.

In some embodiments one of $R_1$ and $R_2$ include a carbonyl or hydroxyl substituent and the other includes an optionally substituted phenyl ring.

In some embodiments, the compounds of formula (I) are selected from those in Table 1.

TABLE 1

| Compound | $R_1$ | $R_2$ |
|---|---|---|
| 1 | —C(O)H | —CH$_3$ |
| 2 | —CH$_2$—CH$_2$—CH$_2$—CH$_2$— ||
| 3 | —CH=CH—CH=CH— ||
| 4 | —N=CH—CH=CH— ||
| 5 | -Ph | -Ph |
| 6 | —CO$_2$H | —CH$_3$ |
| 7 | —C(O)NH$_2$ | —CH$_3$ |
| 8 | —CO$_2$H | —CH$_2$CH$_3$ |
| 9 | —C(O)NH$_2$ | —CH$_2$—CH$_3$ |
| 10 | —CO$_2$H | —CH(CH$_3$)$_2$ |
| 11 | —C(O)NH$_2$ | —CH(CH$_3$)$_2$ |
| 12 | —C(O)CH$_3$ | —CH$_3$ |
| 13 | -Ph | —CH$_3$ |
| 14 | -Ph | —C(O)H |
| 15 | -Ph-4-OCH$_3$ | —C(O)H |
| 16 | —C(O)CH$_2$CH$_2$— ||
| 17 | —C(O)CH$_2$CH$_2$CH$_2$— ||
| 18 | -Ph-4-F | —CO$_2$H |
| 19 | —CH=CH—CF=CH— ||
| 20 | —CH=CH—C(OCH$_3$)=CH— ||
| 21 | -Ph-4-F | -Ph-4-F |
| 22 | —C(O)CF$_3$ | -Ph |
| 23 | -Ph-4-F | —CH$_3$ |
| 24 | -Ph-4-OCH$_3$ | —CH$_3$ |
| 25 | -Ph | —CO$_2$H |
| 26 | -Ph | —C(O)NH$_2$ |
| 27 | -Ph | —C(O)CH$_3$ |
| 28 | -Ph-4-F | —C(O)H |
| 29 | -Ph-4-F | —C(O)NH$_2$ |
| 30 | -Ph-4-OCH$_3$ | —C(O)NH$_2$ |
| 31 | -Ph | —CH$_2$OH |
| 32 | -Ph-4-OCH$_3$ | —CH$_2$OH |

The compounds listed in Table 1 may be isomeric in that the substituent listed as $R_1$ may be substituted at $R_2$ and the substituent listed as $R_2$ may be substituted at $R_1$.

In some cases, the furoxans of the invention are able to isomerize between the 2-N-oxide and 5-N-oxide compounds as shown in Scheme 1:

Scheme 1

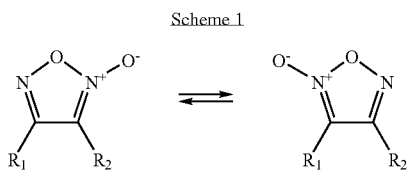

(Katritsky & Rees, *Comprehensive Heterocyclic Chemistry*, 1984, 6, 403-404, Pergammon Press; Advances in Heterocyclic Chemistry, 1981, 29:289-297).

In one aspect of the invention there is provided compounds of formula (I) as described above.

The furoxan compounds used in the present invention may be synthesized by methods known in the art (Katritsky & Rees, *Comprehensive Heterocyclic Chemistry*, 1984, 6, 420-425, Pergammon Press; Advances in Heterocyclic Chemistry, 1981, 29:270-284). Monocyclic furoxans may be prepared by, for example, oxidation of α-dioximes, dehydration of α-nitro ketone oximes, dimerization of nitrile oxides, nitration of 1,2-dialkylvinyl azides, loss of nitrous acid from nitrolic acids and by reaction of olefins and nitrogen oxides. Benzofuroxans and other aromatic ring fused furoxans are commonly prepared by pyrolysis of ortho-nitrophenylazides, oxidation of ortho-nitroanilines and oxidation of ortho-quinone dioximes. Cycloalkyl fused furoxans can be prepared by reacting an α-bromo cyclic ketone with hydroxylamine followed by oxidation or by treating a cyclic 1,3-dione with sodium nitrite followed by hydroxylamine, the resulting trioxime can be then be treated with sodium hypobromide to form the fused furoxan.

In some cases, asymmetric isomeric furoxans may be prepared selectively by oxidation of geometric isomers of the starting asymmetric dioximes. an example of such a reaction is given in Scheme 2.

Scheme 2

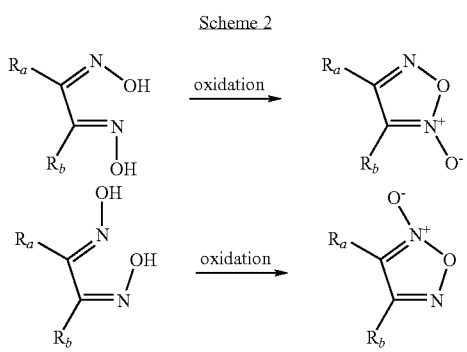

This reaction tolerates a variety of substituents as $R_a$ and $R_b$. For Example, $R_a$ and $R_b$ may be independently alkyl, aryl, acyl, amino and halogen. Such substituents may be optionally further derivatised after formation of the furoxan ring.

For example, an appropriate α,β-unsaturated aldehyde may be reacted with sodium nitrite in mild acid as shown in Scheme 3:

Scheme 3

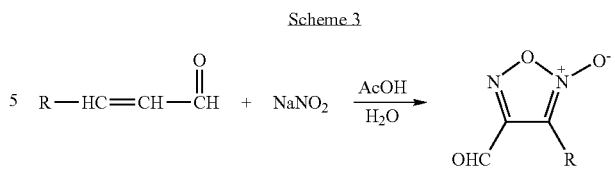

(*J. Heterocyclic Chem.*, 1989, 29(5):1345-47)

The aldehyde may be further elaborated by methods known in the art, for example, oxidation to a carboxylic acid and optional reaction with an alkyl or aryl group to provide an ester or an amino group to provide an amide. Another option is to form an acid chloride followed by further reaction with an alkyl or aryl group to form an acyl group or reaction with an amine to form an amide group. A further option is to react the aldehyde group with an amino group to form an imine which may be optionally reduced. Another option, especially when R is aromatic, is to react the aldehyde with an allylic alcohol.

Another means of preparing furoxan compounds is nitric acid oxidation of substituted acetophenone compounds as shown in Scheme 4:

Scheme 4

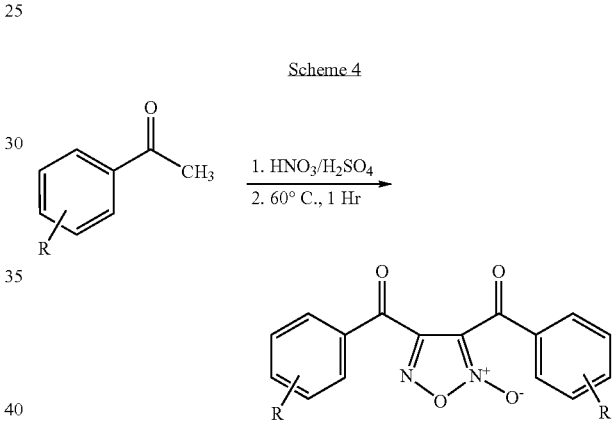

(Nitrode et al., *Bioorg Med. Chem. Lett.*, 2006, 16:2299-2301)

Other syntheses of furoxans are also known. (Cerecetto and Porcal, *Mini-reviews in Medicinal Chemistry*, 2005, 5:57-71).

In some embodiments, the NO donor is a compound of formula (II):

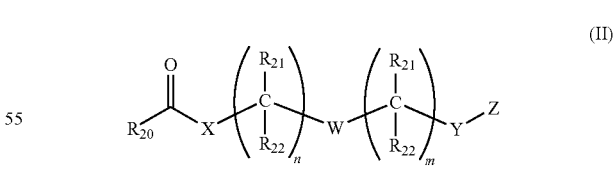

(II)

X is a covalent bond, —O—, —S— or —N($R_{23}$)—;
W is a covalent bond, —O—, —S—, —N($R_{23}$)— or —$C_6H_4$—;
Y is a covalent bond, —O— or —S—;
Z is —NO or —$NO_2$
$R_{20}$ is hydrogen, —OH, —Oalkyl, —$NH_2$, —NHalkyl or —N(alkyl)$_2$;
each $R_{21}$ and $R_{22}$ is independently selected from hydrogen, alkyl, alkenyl, alkynyl, cycloalkyl, halo, hydroxyl, alkyloxy, —CO$_2$H, —CO$_2$alkyl, —CONH$_2$, —CONHalkyl, —CON(alkyl)$_2$, aryl, heterocyclyl and heteroaryl;

R$_{23}$ is a hydrogen or alkyl;

n is 0 or an integer of 1-10; and m is an integer of 1-10.

In some embodiments, one or more of the following applies

X is a covalent bond, —O—, —S—, especially a covalent bond or —O—,

W is a covalent bond, —O—, —S— or —C$_6$H$_4$—, especially a covalent bond or —O—; more especially a covalent bond Y is a covalent bond or —O—, especially —O—;

Z is NO$_2$;

R$_{20}$ is hydrogen, —OH or NH$_2$; especially —OH;

each R$_{21}$, and R$_{22}$ is hydrogen, alkyl, hydroxyl or alkoxy; especially hydrogen;

R$_{23}$ is hydrogen; and n+m is an integer from 3-7, especially 4.

In a particular embodiment, the NO donor is a compound of (II) in which R$_{20}$ is —OH, X is a covalent bond, W is a covalent bond, Y is —O—, Z is NO$_2$, each R$_{21}$ and R$_{22}$ is hydrogen and m+n is an integer from 3-7, especially 5-nitratopentanoic acid.

In one aspect of the invention there is provided compounds of formula (II) as described above.

These nitrato compounds may be prepared by methods known in the art. For example a suitable bromoalkyl carboxylic acid can be reacted with a nitrate salt such as silver nitrate under anhydrous conditions, as described in EP 0984012 A2.

In accordance with the present invention, an NO donor is administered at a level that enhances NO and that does not alter normal systemic vascular tone in the subject. Suitably, the level of NO is a sub-normovasodilatory (SNV) concentration that ranges from about ½ to about $10^{-15}$ of a reference concentration required to induce vasodilation in an anatomical site of a reference subject lacking a vascular condition, which is suitably the neuropathic condition. Vasodilation may be measured using any suitable technique for defining SNV concentrations. Illustrative methods for measuring vasodilation include, but are not limited to, measuring systolic blood pressure (e.g., in a limb or tail), by measuring blood flow in ears or using the vasodilation assay described in Pharmacol Res. 39(3): 217-20 (1999). In a specific embodiment, systolic blood pressure is measured in normotensive experimental animals (e.g., rats) that are lightly sedated via intraperitoneal injection of Zoletil (tiletamine 15 mg/kg, zolazepam 15 mg/kg), using an inflatable tail-cuff. Representative SNV concentration ranges include from about ½ to about ⅟$_{20}$, ½ to about ⅟$_{50}$, ½ to about $10^{-1}$, $10^{-1}$ to about $10^{-15}$, $10^{-2}$ to about $10^{-15}$, $10^{-3}$ to about $10^{-15}$, $10^{-4}$ to about $10^{-15}$, $10^{-5}$ to about $10^{-15}$, $10^{-6}$ to about $10^{-15}$, $10^{-2}$ to about $10^{-13}$, $10^{-2}$ to about $10^{-12}$, $10^{-2}$ to about $10^{-11}$, $10^{-2}$ to about $10^{-10}$, $10^{-2}$ to about $10^{-9}$, $10^{-2}$ to about $10^{-8}$, $10^{-2}$ to about $10^{-7}$, or $10^{-2}$ to about $10^{-6}$ of the reference concentration. In some embodiments in which the NO donor is in slow-release form, the amount of NO donor that is administered as a bolus is in the range of 0.000001 nmol/kg to 2 nmol/kg, 0.00001 nmol/kg to 2 nmol/kg, 0.0001 nmol/kg to 2 nmol/kg, 0.001 nmol/kg to 2 nmol/kg, 0.001 nmol/kg to 1 nmol/kg, 0.001 nmol/kg to 0.6 nmol/kg, 0.004 nmol/kg to 0.4 nmol/kg, preferably in a range selected from 0.005 nmol/kg to 0.3 nmol/kg, 0.006 nmol/kg to 0.2 nmol/kg, 0.007 nmol/kg to 0.1 nmol/kg, 0.008 nmol/kg to 0.09 nmol/kg, 0.009 nmol/kg to 0.08 nmol/kg, 0.01 nmol/kg to 0.07 nmol/kg, 0.02 nmol/kg to 0.06 nmol/kg, and especially 0.03 nmol/kg to 0.05 nmol/kg. In other embodiments in which the NO donor is formulated in a sustained release formulation, the NO donor is adapted to release nitric oxide at a rate of 0.00001 nmol/kg/hour to 2.0 nmol/kg/hour, 0.0001 nmol/kg/hour to 2.0 nmol/kg/hour, 0.0002 nmol/kg/hour to 2.0 nmol/kg/hour or in a range selected from 0.001 nmol/kg/hour to 1.0 nmol/kg/hour, 0.005 nmol/kg/hour to 1.0 nmol/kg/hour, 0.001 nmol/kg/hour to 0.5 nmol/kg/hour, 0.002 nmol/kg/hour to 0.2 nmol/kg/hour, 0.005 nmol/kg/hour to 0.1 nmol/kg/hour, or 0.01 nmol/kg/hour to 0.05 nmol/kg/hour. In illustrative examples of this type, the NO donor is a transdermal patch adapted to release 0.5 nmol to 500 nmol, especially 10 nmol to 100 nmol, more especially 20 nmol to 60 nmol and even more especially about 50 nmol over 6, 9, 12, 18, 24 or 30 hours.

Advantageously, in some embodiments, particularly embodiments where the NO donor is a furoxan NO donor, the NO donor may be used in a manner that minimizes analgesic tolerance development. While tolerance to the analgesic effects of NO donors may occur upon continuous dosing, upon ceasing dosing the analgesic sensitivity to the NO donor returns to normal allowing further administration at original low levels observed in a naive patient. In a clinically relevant setting, where a subject would be dosed on an intermittent dosing schedule, such as once daily, twice daily or three times daily, even over an extended period of time, tolerance to the NO donor is likely to be minimized. This is in contrast to the use of traditional opioid analgesics where tolerance develops with long term administration and the subject requires ever increasing doses.

In some embodiments, the NO donor is a compound that is a slow release nitric oxide donor, releasing NO over an extended period of time after administration. Such a nitric oxide donor maintains a very low level of nitric oxide in the blood stream. The slow release nitric oxide donor may deliver NO at a rate of 0.000001 nmol/Kg/hr to 2.0 nmol/Kg/hr.

In some embodiments, the NO donor is a compound that is a low-release nitric oxide donor, releasing a low concentration of NO into the blood stream by rapid or immediate release of the NO or by a graduated release where the release rate of NO is not constant or by slow-release of the NO. The low-release NO donor may deliver NO to the blood stream of a concentration of $10^{-2}$ to $10^{-15}$ of a reference concentration required to induce vasodilation in an anatomical site of a reference subject lacking vascular condition. For example, the low-release NO donor may be administered as a bolus in the range of 0.000001 nmol/Kg to 2 nmol/Kg.

Suitably, the level of NO donor administered is effective for treating or preventing a neuropathic condition, including a peripheral neuropathic condition such as PDN or a related condition, and especially for the treatment or prevention of pain in neuropathic conditions, including the prevention of incurring pain, holding pain in check, and/or treating existing pain. Whether pain has been treated is determined by measuring one or more diagnostic parameters which is indicative of pain (e.g., subjective pain scores, tail-flick tests and tactile allodynia) compared to a suitable control. In the case of an animal experiment, a "suitable control" is an animal not treated with the nitric oxide donor, or treated with the pharmaceutical composition without nitric oxide donor. In the case of a human subject, a "suitable control" may be the individual before treatment, or may be a human (e.g., an age-matched or similar control) treated with a placebo. In accordance with the present invention, the treatment of pain includes and encompasses without limitation: (i) preventing pain experienced by a subject which may be predisposed to the condition but has not yet been diagnosed with the condition and, accordingly, the treatment constitutes prophylactic treatment for the pathologic condition; (ii) inhibiting pain initiation or a painful condition, i.e., arresting its development; (iii) relieving pain, i.e., causing regression of pain initiation or a painful condition; or (iv) relieving symptoms resulting from a disease or condition believed to cause pain, e.g., relieving the sensation of pain without addressing the underlying disease or condition.

In some embodiments, the NO donor may be administered in combination with, simultaneously in one composition or in separate compositions, or separately and sequentially, with another treatment for neuropathic pain, especially when the NO donor is a furoxan NO donor of formula (I). In some embodiments, the other treatment for neuropathic pain is not an opioid analgesic such as morphine. In some embodiments, the other treatment for neuropathic pain is selected from one or more of anticonvulsants such as carbamazepine, gabapentin, phenyloin, pregabalin and valproate; antidepressants such as amitriptyline, desipramine and duloxetine; central $\alpha$-2 adrenergic agonists such as clonidine and tizanidine; corticosteroids such as dexamethasone and prednisone; NMDA-receptor antagonists such as memantin and dextromethorphan, oral sodium channel blockers such as mexiletine or topical compositions such as capsaicin, EMLA® and lidocaine; or other compositions including baclofen and pamidronate.

In some embodiments, the NO donor is administered without the need for administration of an opioid analgesic. In other embodiments, particularly when the NO donor is a furoxan NO donor of formula (I), the NO donor may be administered in combination with, simultaneously in one composition or in separate compositions, or separately and sequentially, with an opioid analgesic, especially a $\mu$-opioid analgesic, such as morphine.

3. NO Donor-Containing Compositions

Another aspect of the present invention provides compositions for producing analgesia and especially for treating, preventing and/or alleviating the painful symptoms of a neuropathic condition. These analgesic compositions generally comprise at least one NO donor at a level that enhances NO and that does not alter normal systemic vascular tone in the subject, as broadly described above. The effect of the compositions of the present invention may be examined by using one or more of the published models of pain/nociception or of neuropathy, especially peripheral neuropathy, and more especially PDN, known in the art. This may be demonstrated, for example using an animal model which assesses the onset and development of tactile allodynia, the defining symptom of PDN, as for example described herein. The analgesic activity of the compounds of this invention can be evaluated by any method known in the art. Examples of such methods are the Tail-flick test (D'Amour et al. 1941, *J. Pharmacol. Exp. and Ther.* 72: 74-79); the Rat Tail Immersion Model, the Carrageenan-induced Paw Hyperalgesia Model, the Formalin Behavioral Response Model (Dubuisson et al. 1977, *Pain* 4: 161-174), the Von Frey Filament Test (Kim et al. 1992, *Pain* 50: 355-363), the Chronic Constriction Injury, the Radiant Heat Model, and the Cold Allodynia Model (Gogas et al. 1997, *Analgesia* 3: 111-118), the paw pressure test of mechanical hyperalgesia (Randall and Selitto, 1997, *Arch Int Pharmacodyn* 111: 409-414; Hargreaves et al. 1998, *Pain,* 32: 77-88). An in vivo assay for measuring the effect of test compounds on the tactile allodynia response in a rat model of painful diabetic neuropathy is described in Example 1. Compositions which test positive in such assays are particularly useful for the treatment or prevention of neuropathic pain.

The NO donors may be provided as salts with pharmaceutically compatible counterions. Pharmaceutically compatible salts may be formed with many acids, including but not limited to hydrochloric, sulfuric, acetic, lactic, tartaric, maleic, succinic, etc. Salts tend to be more soluble in aqueous or other protonic solvents that are the corresponding free base forms.

The dose of NO donor administered to a patient should be sufficient to achieve a beneficial response in the patient over time such as a reduction in, or relief from, pain, especially neuropathic pain. The quantity of the compound(s) to be administered may depend on the subject to be treated inclusive of the age, sex, weight and general health condition thereof. This quantity, however, will be one that enhances NO and that does not alter normal systemic vascular tone in the subject. In this regard, precise amounts of the NO donor(s) for administration will depend on the judgement of the practitioner. In determining the effective amount of the NO donor(s) to be administered in the production of analgesia, the physician may evaluate severity of the pain symptoms associated with nociceptive or inflammatory pain conditions or numbness, weakness, pain, loss of reflexes and tactile allodynia associated with neuropathic conditions, especially peripheral neuropathic conditions such as PDN. In any event, those of skill in the art may readily determine suitable dosages of the nitric oxide donors of the invention without undue experimentation.

In some embodiments, and dependent on the intended mode of administration, the NO donor-containing compositions will generally contain about 0.001% to 90%, about 0.1% to 50%, or about 1% to about 25%, by weight of NO donor, the remainder being suitable pharmaceutical carriers and/or diluents etc. The dosage of the nitric oxide donor can depend on a variety of factors, such as the individual nitric oxide donor, mode of administration, the species of the affected subject, age and/or individual condition.

Depending on the specific neuropathic condition being treated, the NO donor(s) may be formulated and administered systemically, topically or locally. Techniques for formulation and administration may be found in "Remington's Pharmaceutical Sciences," Mack Publishing Co., Easton, Pa., latest edition. Suitable routes may, for example, include buccal, sublingual, oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the therapeutic agents of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Alternatively, the compositions of the invention can be formulated for local or topical administration. In this instance, the subject compositions may be formulated in any suitable manner, including, but not limited to, creams, gels, oils, ointments, solutions and suppositories. Such topical compositions may include a penetration enhancer such as benzalkonium chloride, digitonin, dihydrocytochalasin B, capric acid, increasing pH from 7.0 to 8.0. Penetration enhancers which are directed to enhancing penetration of the active compounds through the epidermis are advantageous in this regard. Alternatively, the topical compositions may include liposomes in which the active compounds of the invention are encapsulated.

The compositions of this invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as nonionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the NO donor(s) can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for buccal or sublingual administration or oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in watersoluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for buccal, sublingual or oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterise different combinations of active compound doses.

For buccal or sublingual administration, the formulations of the invention can be provided in the form of a tablet, patch, troche, or in free form, such as a gel, ointment, cream, or gum. Examples of suitable buccal or sublingual formulations and devices are disclosed, for example, in U.S. Pat. Nos. 5,863,555, 5,849,322, 5,766,620, 5,516,523, 5,346,701, 4,983,395, and 4,849,224. Such formulations and devices can use a suitable adhesive to maintain the device in contact with the buccal mucosa. Examples of suitable adhesives are found, for example, in U.S. Pat. Nos. 3,972,995, 4,259,314, 4,680,323; 4,740,365, 4,573,996, 4,292,299, 4,715,369, 4,876,092, 4,855,142, 4,250,163, 4,226,848, and 4,948,580. Typically, the adhesive comprises a matrix of a hydrophilic, e.g., water soluble or swellable, polymer or mixture of polymers that can adhere to a wet, mucous surface. These adhesives can be formulated as ointments, thin films, tablets, troches, and other forms. Other non-limiting buccal or sublingual formulations are disclosed in U.S. Pat. Nos. 7,067,116; 7,025,983; 6,923,981; 6,596,298; 6,726,928; 6,709,669; 6,509,040; 6,413,549; 5,976,577; 5,827,541; 5,738,875; 5,648,093; 5,631,023; 5,188,825; 4,020,558; 4,229,447; 3,972,995; 3,870,790; 3,444,858; 2,698,822; 3,632,743, and U.S. Published Application Nos. 20070059361; 20040247648; 20040131661; and 20040028730. In some embodiments, the dosage forms are prepared using pharmaceutically acceptable excipients. Illustrative excipients that are commonly formulated into buccal and sublingual dosage forms include maltodextrin, colloidal silicon dioxide, starch, starch syrup, sugar and α-lactose.

Pharmaceuticals which can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the NO donors may also include injecting or implanting controlled releasing devices designed specifically for this purpose or other forms of implants modified to act additionally in this fashion. Controlled release of an active compound of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres.

The NO donors may be administered over a period of hours, days, weeks, or months, depending on several factors, including the severity of the neuropathic condition being treated, whether a recurrence of the condition is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The compositions of the present invention may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 micrometers, suitably less than 10 micrometers.

In some embodiments, the NO donor may be administered in a composition with another treatment for neuropathic pain. In some embodiments, the other treatment for neuropathic pain is not an opioid analgesic such as morphine. In some embodiments, the other treatment for neuropathic pain is selected from one or more of anticonvulsants such as carbamazepine, gabapentin, phenyloin, pregabalin and valproate; antidepressants such as amitriptyline, desipramine and duloxetine; central α-2 adrenergic agonists such as clonidine and tizanidine; corticosteroids such as dexamethasone and prednisone; NMDA-receptor antagonists such as memantin and dextromethorphan, oral sodium channel blockers such as mexiletine or topical compositions such as capsaicin, EMLA® and lidocaine; or other compositions including baclofen and pamidronate. In some embodiments, particularly when the NO donor is a furoxan NO donor of formula (I), the NO donor is administered in a composition with an opioid analgesic, especially a μ-opioid analgesic such as morphine.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

In order that the invention may be readily understood and put into practical effect, particular preferred embodiments will now be described by way of the following non-limiting examples.

EXAMPLES

Example 1

Anti-Allodynic Efficacy and Potency of the NO Donor Compound 1

Preparation of Compound 1

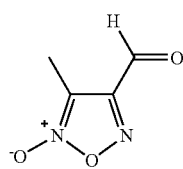

Compound 1

Compound 1 was prepared by the method a set out in *Journal of Heterocyclic Chemistry,* 1989, 26(5):1345-1347. But-2-ene aldehyde was treated with sodium nitrite in the presence of aqueous acetic acid to provide Compound 1.

Experimental Animals

Adult male Wistar rats (225 g-250 g) were purchased from the Central Animal Breeding House, The University of Queensland (Brisbane, Australia) and were housed in a temperature-controlled environment (21±2° C.) with a 12 h/2 h dark/light cycle; food and water were available ad libitum. Rats were given at least a 24 h acclimatisation period prior to experimentation. Ethics approval for these experiments was obtained from the Animal Experimentation Ethics Committee of The University of Queensland.

Drugs and Materials

Compound 1 was synthesized by Dr Craig Williams, School of Chemistry and Molecular Biosciences, The University of Queensland. Streptozotocin, citric acid, and trisodium citrate were purchased from Sigma-Aldrich Pty Ltd (Sydney, Australia). Morphine hydrochloride powder and vials containing sodium benzylpenicillin (Benpen™) vials containing 600 mg of powder were purchased from the Central Pharmacy of the Royal Brisbane and Womens Hospital (Brisbane, Australia). Morphine sulfate ampoules were obtained from Hameln Pharmaceuticals GmbH (Hameln, Germany). Xylazine (Ilium Xylazil™), Zoletil 100® solution (containing: tiletamine HCl 2.5 mg/mL and zolazepam HCL 2.5 mg/mL), sodium benzylpenicillin (Benpen™) vials containing 600 mg of powder and topical antibiotic powder (containing: neomycin sulphate 2.5 mg, sulfacetamide sodium 100 mg, nitrofurazone 2 mg, phenylmercuric nitrate 0.05 mg and benzocaine 5 mg in 50 g soluble powder) were purchased from Provet Queensland Pty Ltd (Brisbane, Australia). Blood glucose meters (Precision QID, Accucheck advantage 2) and glucose testing electrodes (Precision Plus™ and Accucheck Advantage™) were purchased from the Campus Pharmacy at The University of Queensland (Brisbane, Australia). Medical grade $CO_2$ and $O_2$ were purchased from BOC gases Ltd (Brisbane, Australia) and isoflurane (Isoflo™) was purchased from Abbott Australasia Pty Ltd (Sydney, Australia).

Test and Control Articles

Stock solutions of morphine hydrochloride (26.6 mM) were prepared in distilled water (concentrations expressed as the free base). A stock solution (24 μM) of Compound 1 and subsequent dilutions were prepared in a mixture of DMSO: distilled water (90%:10%). Compound 1 and morphine hydrochloride stock solutions were protected from light and stored at 2-4° C. until required.

Diabetes Induction

Whilst anaesthetized with a mixture of Zoletil 100® (tiletamine HCl 0.625 mg and zolazepam 0.625 mg) and xyalazine HCl (5 mg) administered by intraperitoneal injection to induce deep and stable anaesthesia, adult male Wistar rats were administered single intravenous bolus doses of streptozotocin (STZ, 75 mg/kg) via a cannula surgically inserted into the superior aspect of the bifurcation of the internal and external jugular veins. Following this, the jugular cannula was withdrawn, the vein tied off, and the incision sutured. Following surgery, rats received antibiotic prophylaxis in the form of topical dusting powder over the sutured incisions, as well as a subcutaneous injection of benzylpenicillin (60 mg). Rats were placed in individual cages, kept warm and monitored closely during the surgical recovery period. Rats were classified as diabetic if on day 10 post-STZ administration, their daily water intake was ≥100 mL and their corresponding blood glucose levels (BGLs) were ≥15 mM.

Development of Tactile (Mechanical) Allodynia

Calibrated von Frey filaments were used to document the time course for the development and maintenance of tactile allodynia (defining symptom of PDN). Tactile allodynia was considered to be fully developed when von Frey paw withdrawal thresholds in the hindpaws of STZ-diabetic rats were ≤6 g compared with ~12 g in the same animals prior to the induction of diabetes with STZ.

Test and Control Articles

Antinociceptive Testing

In this present study, the antinociceptive effects of single s.c. bolus dose of Compound 1 and morphine administered to control non-diabetic Wistar rats were defined as "Week 0" and these effects were compared with the corresponding effects produced in STZ-diabetic Wistar rats tested at 10, 14 and 24 weeks post-STZ administration.

Briefly, baseline PWTs were determined for both hindpaws prior to each antinociceptive testing session in the non-diabetic control group at week 0 as well as in groups of STZ-diabetic rats at 10, 14 and 24 wks. Following administration of single subcutaneous (s.c.) bolus doses of the test (Compound 1) or control (morphine, vehicle) articles to groups of STZ-diabetic rats, PWTs were determined at the following post-dosing times: 0.25, 0.5, 0.75, 1, 1.25, 1.5, 2 and 3 h.

Figure 1:
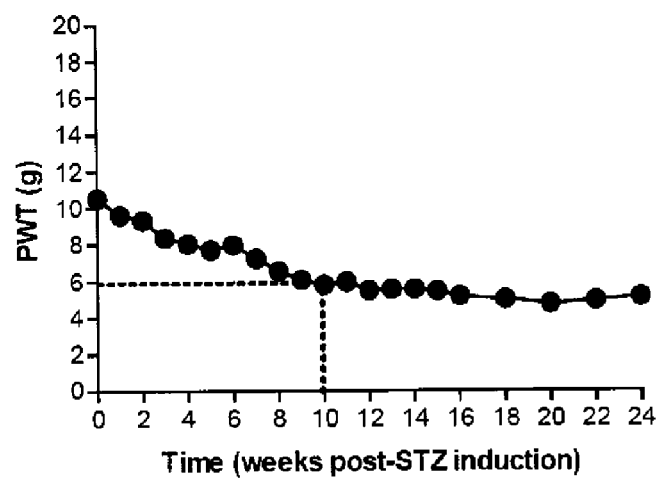
FIG. 1 is a graphical representation showing that tactile (mechanical) allodynia is fully developed by ~9-10 wks post-STZ administration in adult male Wistar rats.

Tactile (mechanical) allodynia was fully developed in the hindpaws of STZ-diabetic Wistar rats by ~9-10 wks post-STZ administration (FIG. 1).

The PWT vs time data were normalized by subtracting the pre-dosing baseline PWT values for each individual rat to obtain $\Delta$PWT values as follows: Normalized ($\Delta$)PWT value=Post-treatment PWT value−PWT value prior to treatment.

$\Delta$PWT versus time curves were then constructed. Trapezoidal integration was used to estimate $\Delta$PWT AUC values for individual rats in the non-diabetic and STZ-diabetic rat treatment groups. $\Delta$PWT AUC versus dose curves were constructed and GraphPad™ Prism was used to estimate the ~$ED_{50}$ values.

Temporal Development of Morphine Hyposensitivity in STZ-Diabetic Rats

Figure 2:
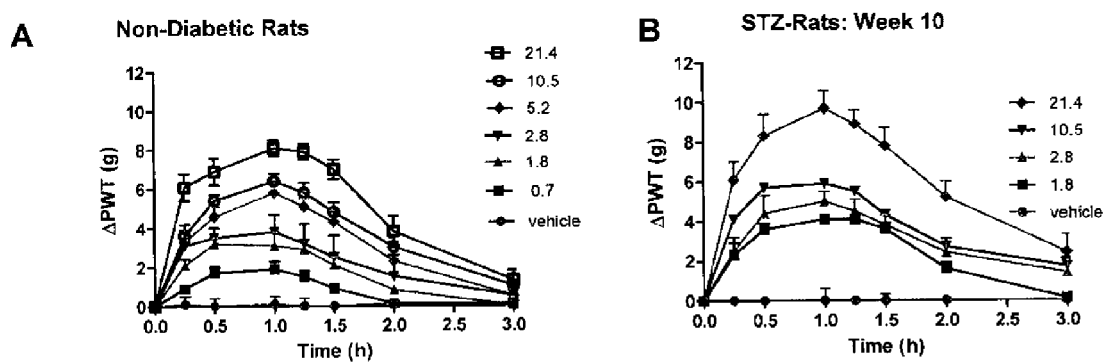
FIG. 2 is a graphical representation showing mean (±SEM) ΔPWT versus time curves produced by single s.c. bolus doses (1.8-21.4 μmol/Kg) of morphine produces dose-dependent (A) antinociception in control non-diabetic rats (n=4-9 per dose), and (B) to (D): anti-allodynia in STZ-diabetic rats at 10 (B; n=4-9 per dose), 14 (C; n=6-10 per dose) and 24 (D; n=4-6 per dose) weeks post STZ administration with temporal development of morphine hyposensitivity across the 24 wk post-STZ study period. By contrast, vehicle (n=3-4) did not produce significant antinociception or anti-allodynia in the hindpaws of either non-diabetic or STZ-diabetic rats respectively.
Figure 2:
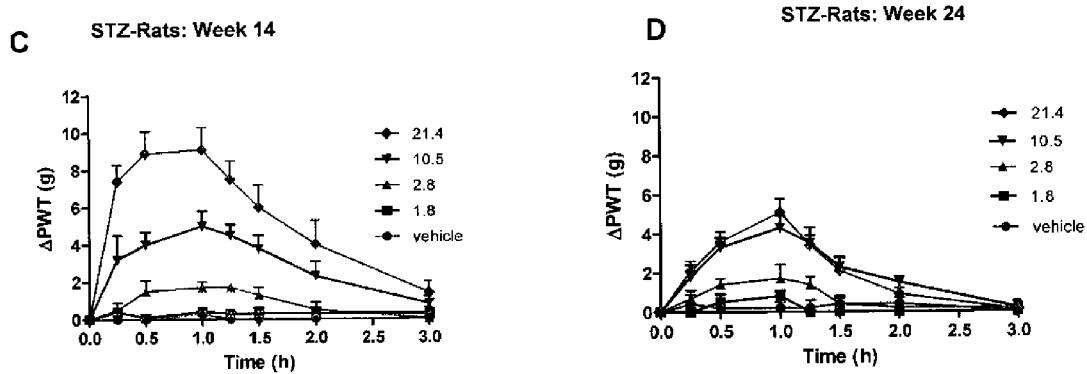

Single s.c. bolus doses of morphine (1.8-21.4 µmol/kg s.c.) produced dose-dependent antinociception in the hindpaws of control non-diabetic rats (FIG. 2A) as well as dose-dependent anti-allodynia in the hindpaws of STZ-diabetic rats (FIG. 2 B-D). The peak effect was observed at ~30-60 min post-dosing with a corresponding duration of action of ~2-3 h (FIG. 2). At week 10 post-STZ administration (FIG. 2B respectively), single bolus doses of morphine at 2.8 µmol/kg fully reversed mechanical allodynia at the time of peak response such that the mean (±SEM) PWT value (10.7±0.6 g) matched that for the hindpaws of non-diabetic rats. By week 14 post-STZ administration, single bolus doses of morphine at 1.8 µmol/kg were no longer effective and the anti-allodynic potency of morphine at 2.8 µmol/kg was significantly reduced (FIG. 2C). However, increasing the dose of morphine 4-fold to 10.5 µmol/kg at week 14 post-STZ administration completely relieved mechanical allodynia in the hindpaws at the time of peak response (FIG. 2C). By week 24 post-STZ administration, the anti-allodynic potency of single s.c. bolus doses of morphine at 10.5 and 21.4 µmol/kg was markedly reduced (FIG. 2D).

These results show the temporal decrease in the potency of morphine administered as single s.c. bolus doses at 10-, 14- and 24-wks post-STZ administration. Specifically, by week 24 post STZ-administration, the mean (±SEM) extent and duration of anti-allodynia ($\Delta$PWT AUC values) produced by the largest dose of morphine administered (21.4 µmol/kg) was similar to that produced by the 10.5 µmol/kg bolus dose of morphine at 14 weeks post-STZ, indicative of marked morphine hyposensitivity in these animals. Hence, it is clear that morphine hyposensitivity developed in a temporal manner as PDN progressed in these STZ-diabetic rats.

Figure 3:
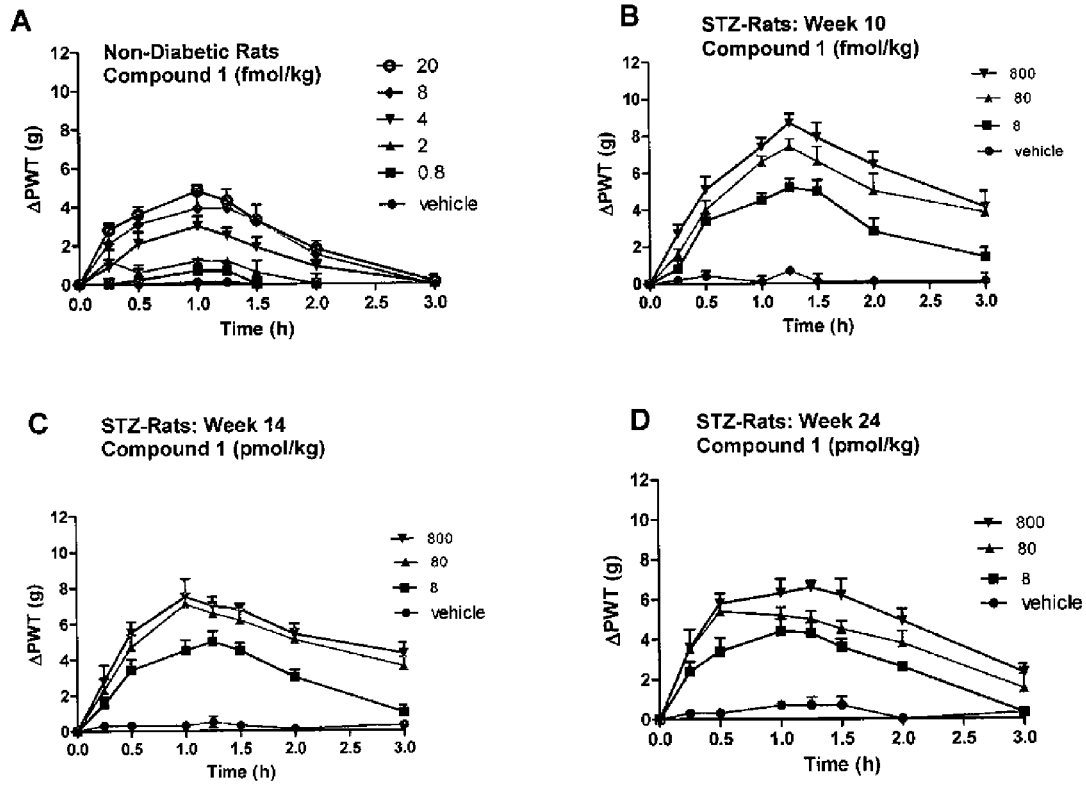
FIG. 3 is a graphical representation showing mean (±SEM) ΔPWT versus time curves produced by single s.c. bolus doses (8-800 pmol/kg) of the furoxan NO donor of formula (I), Compound 1, produces dose-dependent (A) antinociception in non-diabetic rats (0.8-20 fmol/Kg, n=3-10 per dose), and (B) to (D): anti-allodynia/antinociception at 10 (B; n=6-8 per dose), 14 (C; n=7-8 per dose) and 24 (D; n=6-7 per dose) weeks post STZ administration in diabetic rats with an approximately 10,000-fold decrease in potency occurring between 10- and 14-wks post-STZ administration. By contrast, vehicle (n=5-7) did not produce significant antinociception or anti-allodynia in the hindpaws of either non-diabetic or STZ-diabetic rats respectively.

Temporal Changes in the Anti-Allodynic Potency of Compound 1 in STZ-Diabetic Rats Single s.c. bolus doses of Compound 1 (2-20 fmol/kg s.c.) produced dose-dependent antinociception in the hindpaws of control non-diabetic rats (FIG. 3A). Administration of single s.c. bolus doses of Compound 1 at 10-, 14- and 24-wks post-STZ administration produced dose-dependent anti-allodynia/antinociception in the rat hindpaws (FIG. 3 B-D) but the doses required at 14- and 24-wks (8-800 pmol/kg) were ~10,000-fold higher than the effective doses at 10-wks post-STZ administration (8-800 fmol/kg). Specifically, at 10 wks post-STZ administration, the 8 fmol/kg dose produced complete relief of mechanical allodynia at the time of peak effect (FIG. 3B). Peak anti-allodynic responses (PWT: 10.6±0.5 g) were observed at ~75 min post-dosing and the corresponding mean durations of action were >3 h (FIG. 3B). By 14 weeks post-STZ administration (FIG. 3C), the doses of Compound 1 that had been used successfully at week 10 post-STZ administration to fully reverse mechanical allodynia in the hindpaws, were no longer effective. However, increasing the magnitude of the s.c. bolus doses of Compound 1 to 8, 80 and 800 pmol/kg (FIG. 3C), again resulted in dose-dependent anti-allodynia in these animals. Following administration of single s.c bolus doses of Compound 1 at 80 and 800 pmol/kg, mechanical allodynia in the hindpaws of STZ-diabetic rats at 14- (FIG. 3C) and 24-wks (FIG. 3D) post-STZ administration was fully alleviated at the time of peak response such that the mean (±SEM) peak PWT values were similar to baseline PWT values for control non-diabetic rats and the corresponding duration of action was ≥3 h.

These results show the large decrease in the potency of single s.c. bolus doses of Compound 1 at 14 and 24 wks c.f. 10-wks post-STZ administration. Specifically, by week 24 post STZ-administration, the mean (±SEM) extent and duration of anti-allodynia ($\Delta$PWT AUC value) produced by the largest dose of Compound 1 administered (800 pmol/kg) was similar to that produced by the 8 fmol/kg bolus dose of Compound 1 at 10-wks post-STZ in these animals. At 24 weeks post-STZ administration, the bolus doses of Compound 1 that were effective at 14 weeks post-STZ administration continued to evoke dose-dependent anti-allodynia with only a small decrease in $\Delta$PWT AUC values relative to the corresponding values determined at week 14 post-STZ administration.

Example 2

Effects of the NO Donor Compound 1 on Systolic Blood Pressure in Normotensive Wistar Rats Experimental Animals Adult male Wistar rats (300 g-350 g) were purchased from UQBR (University of Queensland Biological Resources), The University of Queensland (Brisbane, Australia) and were housed in a temperature-controlled environment (21±2° C.) with a 12 h/12 h dark/light cycle; food and water were available ad libitum. Rats were given at least a 24 h acclimatisation period prior to experimentation. Ethics approval for these experiments was obtained from the Animal Experimentation Ethics Committee of The University of Queensland.

Drugs and Materials

Compound 1 was synthesized by Dr Craig Williams, School of Chemistry and Molecular Biosciences, The University of Queensland. Zoletil 100® solution (containing: tiletamine HCl 2.5 mg/ml and zolazepam HCL 2.5 mg/mL), was purchased from Provet Queensland Pty Ltd (Brisbane, Australia).

Blood Pressure Measurement

Sedation was induced by the intraperitoneal administration of Zoletil® (tiletamine 15 mg $kg^{-1}$ and zolazepam 15 mg $kg^{-1}$). Using a tail pulse transducer (MLT1010) and an inflatable tail cuff with a Capto SP844 physiological pressure transducer (MLT844/D), systolic blood pressure was recorded via a PowerLab data acquisition unit (ADInstruments, Sydney, Australia). Tails were warmed with lukewarm water prior to each blood pressure reading to increase peripheral circulation so as to facilitate blood pressure recordings using the tail cuff method.

This study was designed to assess the effects of single s.c. bolus doses of the furoxan NO donor, Compound 1, relative to vehicle (DMSO:water, 90:10) on systolic blood pressure in normotensive, non-diabetic, adult male Wistar rats. Single bolus doses of Compound 1 were administered by s.c. injection into the back of the neck of adult male normotensive, non-diabetic Wistar rats in the dose range, 80 fmol/kg to 80 lμmol/kg. Specifically, the doses of Compound 1 tested were 80 fmol/kg (n=3), 800 pmol/kg (n=8), 8 nmol/kg (n=6), 800 nmol/kg (n=4), 8 μmol/kg (n=4), 80 μmol/kg (n=3).

Figure 4:
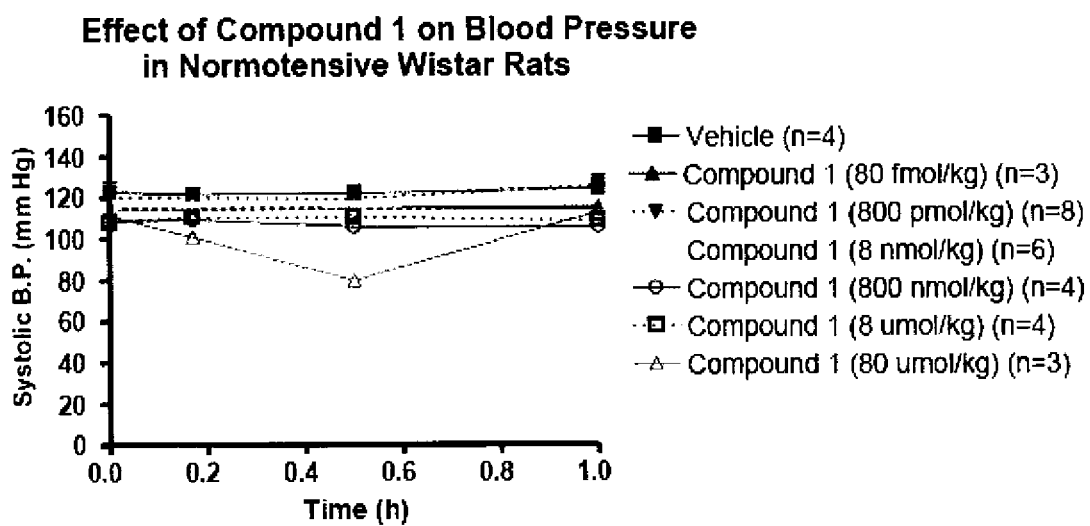
FIG. 4 is a graphical representation showing that neither single s.c. bolus doses of vehicle (DMSO:water, 90:10) nor the furoxan NO donor of formula (I), Compound 1, at 80 fmol/kg-8 μmol/kg, significantly altered mean (±SEM) systolic blood pressure of adult male normotensive non-diabetic Wistar rats for up to 1 h post-dosing. By contrast, single s.c. bolus doses of Compound 1 at 80 μmol/kg to similar animals, significantly reduced systolic blood pressure at 30 min post-dosing relative to pre-dosing baseline measurements of systolic blood pressure.

Following administration of single s.c. bolus doses of the furoxan NO donor, Compound 1, to normotensive non-diabetic adult male Wistar rats, there were no significant effects (p>0.05) on systolic blood pressure for doses in the range, 80 fmol/kg to 8 μmol/kg (FIG. 4). However, at the highest dose tested (80 μmol/kg, n=3), mean (±SEM) systolic blood pressure decreased significantly (p<0.05) from 111.3 (±1.5) mm Hg just prior to administration of Compound 1 (80 μmol/kg) to 79.8 (±0.5) mm Hg at the time of peak effect at 30 min post-dosing (FIG. 4). By 1 h post-dosing, mean systolic blood pressure in the same animals (112.6±0.4 mm Hg) did not differ significantly (p>0.05) from baseline systolic blood pressure determined just prior to dose administration (FIG. 4).

Example 3

Compound 1 Evokes Anti-Allodynia in STZ-Diabetic Wistar Rats

Non-Opioid Mechanism and Partial Activation of sGC

Experimental Animals

Adult male Wistar rats were used as for Example 1 except that they were purchased from UQBR (University of Queensland Biological Resources).

Drugs and Materials

Compound 1 was synthesized by Dr Craig Williams, School of Chemistry and Molecular Biosciences, The University of Queensland (Brisbane, Australia). 1H-[1,2,4]-oxadiazolo[4,3-a]quinoxalin-1-one (ODQ) and naloxone hydrochloride dihydrate were purchased from Sigma-Aldrich Pty Ltd (Sydney, Australia). Stock solutions of naloxone hydrochloride (30.6 mM) were prepared in distilled water (concentrations expressed as the free base). Fresh solutions of ODQ (53.4 mM) in DMSO were prepared for each experiment.

Method

Allodynia was assessed using calibrated von Frey filaments as described in Example 1.

As most studies indicate that the biological effects of NO are mediated primarily via activation of soluble guanylyl cyclase (sGC) to increase cellular levels of cGMP, the contribution of NO/sGC/cGMP signaling to the anti-allodynic effects of Compound 1 was assessed. Briefly, 14-18 week STZ diabetic rats were pre-treated with a single bolus dose of ODQ (53.4 μmol·kg s.c.), a selective inhibitor of sGC at 60 min prior to administration of single bolus doses of Compound 1 (800 pmol/kg s.c.). Von Frey PWTs in the hindpaws were determined prior to ODQ administration and at the following times post-ODQ administration, 0.5, 1 hour (immediately prior to Compound 1 dosing), 1.25, 1.5, 1.75, 2, 2.5, 3, 3.5 and 4 hours.

To examine the possible involvement of opioid receptors in mediating the anti-allodynic/antinociceptive effects of Compound 1, the non-specific opioid receptor antagonist, naloxone, was employed. Briefly, single s.c. bolus doses of the non-selective opioid antagonist, naloxone (1.25 μmol/kg), were administered 10 minutes prior to single s.c. bolus doses of Compound 1 (800 pmol/kg) to 14-18 week STZ-diabetic rats. For comparative purposes, naloxone-pretreated 14-18 week STZ-diabetic received single s.c. bolus doses of morphine (7 μmol/kg) instead of Compound 1.

Compound 1 Evokes Anti-Allodynia in STZ-Diabetic Wistar Rats

Non-Opioid Mechanism

Figure 5A:
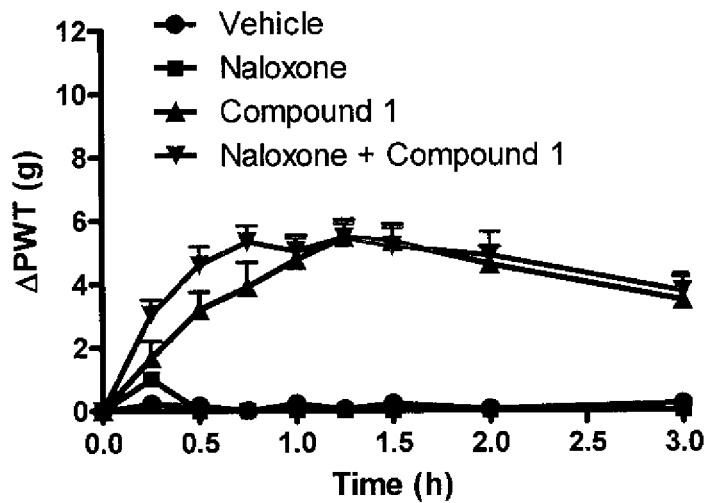
FIG. 5 is graphical representations showing mean (±SEM) ΔPWT versus time curves in 14-18 week STZ-diabetic rats produced by single s.c. bolus doses of (A) Compound 1 (800 pmol/Kg) (black upward closed triangles, n=6), naloxone (1.25 μmol/Kg) at 10 minutes prior to Compound 1 (800 pmol/Kg) (grey downward closed triangles, n=6), naloxone (1.25 μmol/Kg) (black closed squares, n=2) and vehicle (grey closed circles, n=6) or (B) morphine (7 μmol/Kg) (black upward closed triangles, n=6), naloxone (1.25 μmol/Kg) at 10 minutes prior to morphine (7 μmol/Kg) (grey downward closed triangles, n=7), naloxone (1.25 μmol/Kg) (black closed squares, n=2) and vehicle (grey closed circles, n=2) showing that in 14-18 week STZ-diabetic rats pretreated with naloxone (1.25 μmol/Kg s.c.) at 10 minutes prior to either Compound 1 (800 pmol/Kg s.c.) or morphine (7 μmol/Kg s.c.) the anti-allodynic effects of morphine were attenuated by naloxone (as expected) whereas the anti-allodynic effects of Compound 1 were naloxone insensitive. (C) By contrast the anti-allodynic effects of single s.c. bolus doses of Compound 1 (800 pmol/Kg) in 14-18 wk STZ-diabetic rats were partially sensitive to pre-treatment with single s.c. bolus doses of ODQ (53 μmol/Kg) administered at 60 minutes prior to administration of Compound 1 [ODQ and Compound 1, grey solid squares; vehicle and Compound 1, black solid circles; vehicle and ODQ, black solid triangles].
Figure 5B:
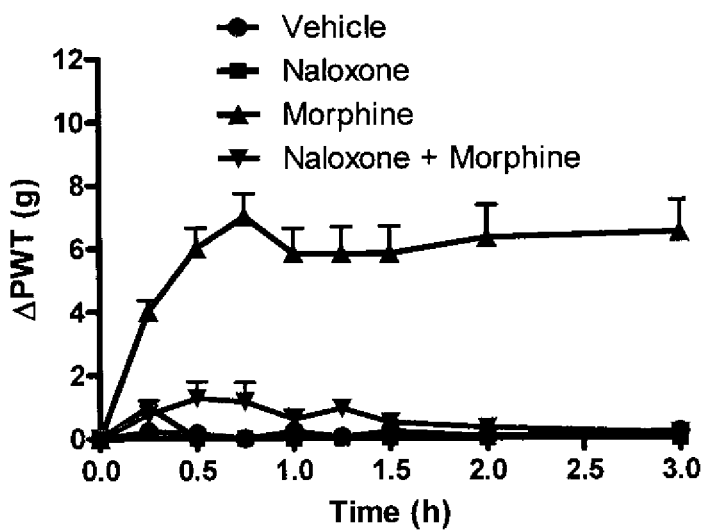

Pre-treatment of 14-18 wk STZ-diabetic rats with single bolus doses of naloxone (1.25 μmol/kg s.c.) 10 min before administration of single bolus doses of Compound 1 (800 pmol/kg s.c.) did not significantly attenuate (P>0.05) the extent and duration of anti-allodynia (ΔPWT AUC values) compared with vehicle-pretreated STZ-diabetic rats administered bolus doses of Compound 1 at 800 pmol/kg (FIG. 5A) such that the mean (±SEM) ΔPWT AUC values did not differ significantly (P>0.05) between the two groups. Importantly, pre-treatment of 14-wk STZ-diabetic rats with naloxone (1.25 μmol/kg s.c.) 10 min prior to single bolus doses of morphine at 7 μmol/kg s.c., completely abolished the anti-allodynic effects of morphine relative to vehicle pre-treated STZ-diabetic rats administered the same dose of morphine (FIG. 5B). Together, these findings indicate that although the anti-allodynic effects of the prototypic μ-opioid agonist, morphine, were opioid-receptor mediated, the anti-allodynic effects of Compound 1 in STZ-diabetic rats were not.

Compound 1 Anti-Allodynia in STZ-Diabetic Wistar Rats

Partial Activation of sGC

Figure 5C:
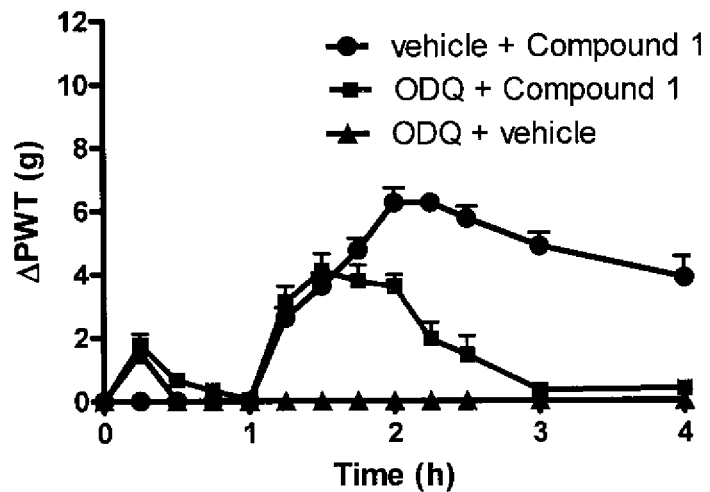
Figure 6A:
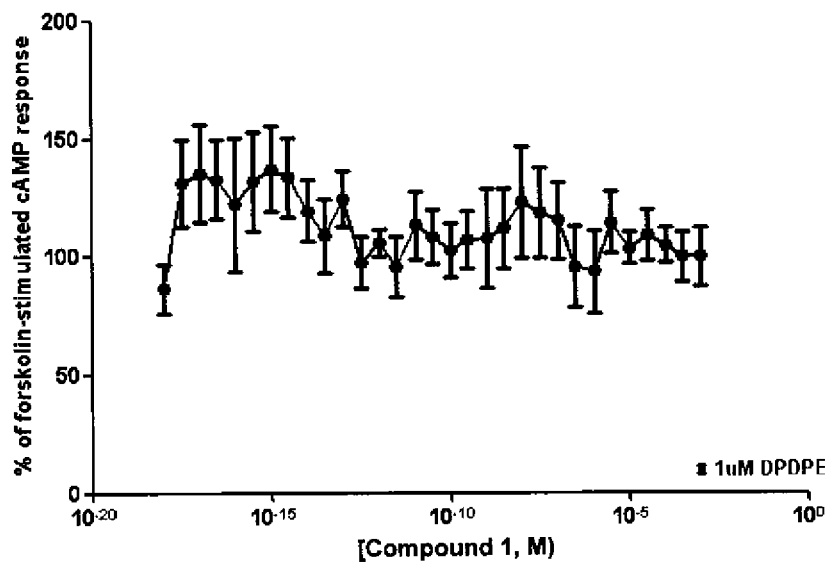
FIG. 6 provides graphical representations showing the effects of Compound 1 on forskolin-stimulated cAMP responses in (A) delta opioid receptor (DOP)-transfected HEK293 cells (Data are means±SEM., n=4), (B) kappa opioid receptor (KOP)-transfected HEK293 cells (Data are means±SEM., n=4) and (C) untransfected HEK293 cells (Data are means±SEM., n=6).
Figure 6B:
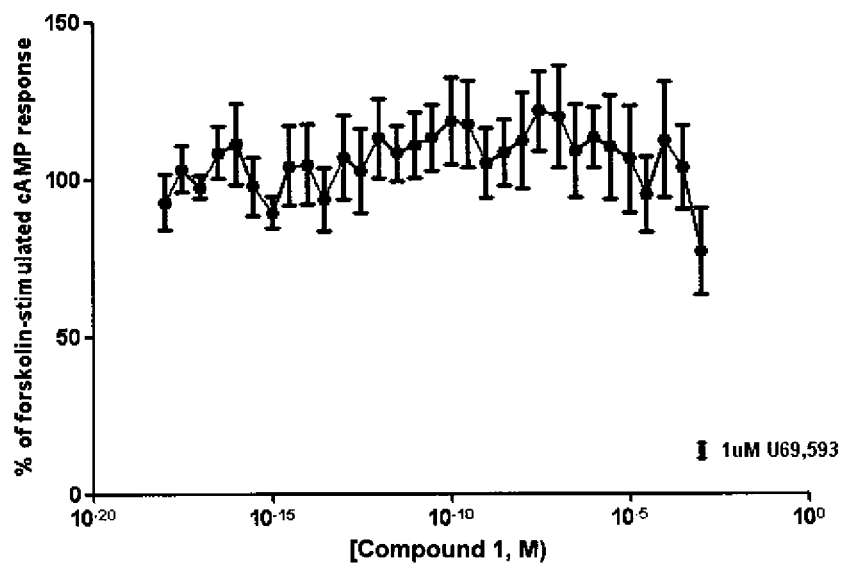
Figure 6C:
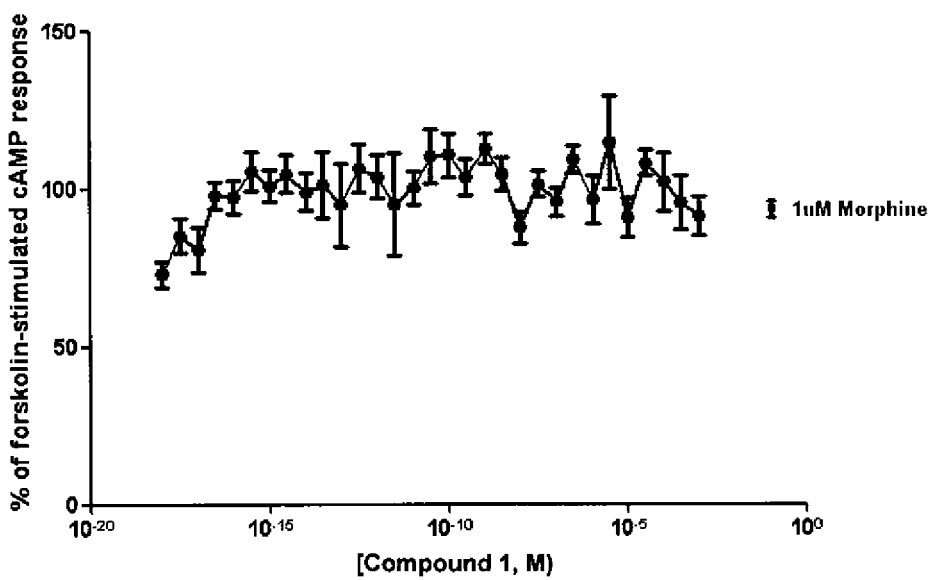

Pre-treatment of 16-wk STZ-diabetic rats with a single bolus dose of ODQ (53.4 μmol/kg s.c.) 60 min prior to a single bolus dose of Compound 1 (800 pmol/kg s.c.) produced a transient increase in mean PWTs in the hindpaws which returned to baseline by 5 min post-dosing. Although ODQ did not significantly attenuate the anti-allodynic effects of Compound 1 (800 pmol/kg) in the first 45 minutes after Compound 1 administration, the anti-allodynic effects of Compound 1 (800 pmol/kg) were significantly attenuated from 45 minutes onwards (FIG. 5C) such that the mean (±SEM) ΔPWT AUC was significantly ($P<0.05$) less than the corresponding value for vehicle-pretreated STZ-diabetic rats administered the same dose of Compound 1. These findings suggest that the anti-allodynic effects of Compound 1 in STZ-diabetic rats are mediated by both cGMP-dependent and independent mechanisms.

Example 4

Absence of Behavioural Side-Effects with Compound 1 in Contrast to Morphine

Even at the highest dose of Compound 1 (800 pmol/kg s.c.) administered to STZ-diabetic rats, there were no discernable side-effects. This was in contrast to morphine which produced staring and sedation at the highest dose tested (21 μmol/kg).

Example 5

Effects of the Furoxan No Donor Compound 1, Morphine or Vehicle on Forskolin-Stimulated Camp Responses in HEK293 Cells Transfected with Opioid Receptors The cellular mechanism of action by which Compound 1 evokes its anti-allodynic effects was investigated using HEK293 cells stably transfected with mouse μ-, δ- or κ-opioid receptors (MOP, DOP and KOP receptors respectively). Non-transfected HEK293 cells were used as a control. Transfected HEK293 cells were maintained in Dulbecco's Modified Eagle's Medium (DMEM) supplemented with 10% fetal bovine serum (FBS) and geneticin (1 mg/mL). Non-transfected HEK293 cells were maintained in DMEM supplemented with 10% FBS.

The functional interaction between opioids and opioid-like compounds and specific opioid G-protein-coupled receptors (GPCRs) was assessed by measuring changes in intracellular cAMP levels relative to basal levels. The Alphascreen cAMP functional assay measures agonist and antagonist activity of GPCRs by stimulating cells to either increase or decrease intracellular cAMP levels. The assay was performed using an Alphascreen cAMP kit according to the manufacturer's instructions.

The assay was performed in a 384 well plate and each data point was performed in triplicate. Compound 1 was analyzed on the same plate as controls and cAMP standards.

Detection of cAMP is based on the competition between intracellular cAMP and biotinylated cAMP linked streptavidin-coated donor beads for anti-cAMP conjugated acceptor beads. When the donor and acceptor beads are in close proximity visible light emitted at 520-620 nm is detected using the Envision multilabel plate reader.

Stocks Solution Preparation 500 mM IBMX Solution 100 mg IBMX was dissolved in 900 μL DMSO to give a 500 mM stock solution. Aliquots were stored at −20° C.

50 mM Forskolin Solution 5 mg forskolin was dissolved in 244 μL of 95% ethanol to give a 50 mM stock solution and was stored at −20° C. and used as required.

Fresh Reagents

The following reagents were prepared fresh in 50 mL conical tubes:

Stimulation Buffer

1×HBSS, 0.1% BSA, 1 mM IBMX

For 50 mL, 5 mL 10×HBSS was added to a 50 mL tube and made up to 50 mL with water. 50 mg BSA was added and the solution allowed to stand at 37° C. until BSA was dissolved then 100 μL of IBMX was added while the buffer was at 37° C. to ensure that the IBMX did not precipitate.

Lysis Buffer 0.3% Tween-20, 5 mM HEPES, 0.1% BSA

For 40 mL, 1.2 mL 10% Tween-20 and 200 μL 1M HEPES were added to a 50 mL tube and made up to 40 mL with water. 50 mg BSA was added and the solution allowed to stand at 37° C. until BSA was dissolved.

Stimulation Buffer with Forskolin

*200 μM in Stimulation Buffer

Forskolin was made up to a dilution of 1:250 from the 50 mM stock and added to the required amount of stimulation buffer. It should be noted that the final concentration in the assay plate will be halved.

Preparation of Compounds

Compound 1

Stock solutions of Compound 1 at 1 mM and 100 μM were prepared in an appropriate diluent and stored at 4° C. Compound 1 was diluted fresh from stock solutions to a working concentration in stimulation buffer with forskolin. It should be noted that as compounds are diluted 1:1 with cells in the assay, the working concentrations are twice the final required concentration.

Control Compounds

Compounds with known activity against MOP, DOP and KOP receptors including morphine, DPDPE and U69,593, respectively were used as control opioid agonists. Control opioid agonists were used at 1 μM and were diluted fresh in stimulation buffer with forskolin from stocks stored at −20° C. For the assay 5 μL of prepared control compounds were added per well in triplicate.

Preparation of Cells

The assay performance was optimized by using cells at low passage number and at 70-90% confluence. The cells were prepared for the assay by removing growth medium, adding Versene and then incubating at 37° C. for approximately 5 minutes to allow cells to detach from the tissue culture plastic. The cells were collected and centrifuged for 2 minutes at 275×g. The supernatant was decanted and the cell pellet resuspended in 1×PBS. The cell concentration was determined using a haemocytometer. The cells were re-centrifuged for 2 minutes at 275×g and the supernatant decanted. The cells were resuspended in stimulation buffer to a final concentration of $1\text{-}4\times10^4$ cells per mL. Note that the cell number will influence the cAMP levels measured before (basal) and after adenylyl cyclase activation. A cell titration was performed to optimize the difference between basal and stimulation levels of cAMP. Cells were incubated in stimulation buffer for 20 to 30 minutes at 37° C. prior to adding 5 µL to wells containing test and control compounds. Note that cells were not added to the cAMP standards.

Preparation of a cAMP Standard Curve

A standard cAMP dilution series was prepared from the kit supplied using 50 µM cAMP solution. The solution was vortexed at maximum intensity for 5 seconds before use then serially diluted to provide a final concentration range from 5 µM to 0.5 nM cAMP (for example: 5 µM, 0.5 µM, 50 nM, 15 nM, 5 nM, 1.5 nM, and 0.5 nM cAMP). A positive control (no cAMP) was also included. For the assay 10 µL of standard dilutions were added per well in triplicate.

Preparation of Acceptor and Donor Bead Solutions

The anti-cAMP conjugated acceptor beads and streptavidin-coated donor beads are light sensitive and need to be handled under subdued lighting or under lights fitted with green filters. Once the beads have been added to the assay plate it should be wrapped in foil so that incubations are performed in the dark. Acceptor and donor bead solutions were prepared in 15 mL conical tubes while the cells were incubating and kept in the dark until required. For the acceptor bead solution, 10 µL bead suspension per mL of lysis buffer was gently mixed. For the donor bead solution 10 µL bead suspension per mL of lysis buffer and 0.75 µL/mL of cAMP-biotin were used and mixed gently.

Camp Assay Procedure

1. Standards (10 µL/well), control compounds (5 µL/well) and Compound 1 (5 µL/well) were added into 384-well plates and sealed with Top Seal adhesive sealing film and left at room temperature until the cell incubation was complete.
2. 5 µl aliquots of cells incubated in stimulation buffer was added to the wells containing Compound 1 and control compounds, but not to the standards. The cells and compounds were incubated for 30 min at 37° C.
3. 10 µL lysis buffer was added per well.
4. Under subdued lighting 5 µL acceptor bead solution was added to each well. The plate was wrapped in foil and incubated at room temperature with gentle mixing on an orbital shaker for 60 min.
5. Also under subdued lighting 5 µL donor bead solution was added to each well, the plate wrapped in foil, and then incubated overnight at room temperature with gentle mixing on an orbital shaker.
6. cAMP levels were measured using an Envision multilabel plate reader.

Results Analysis

The results were analyzed using the Graphpad PRISM® software program to calculate the intracellular levels of cAMP for each triplicate data point and the standard deviation of these data points.

In some assays, cells underwent pre-treatment with pertussis toxin (PTX) (100 ng/mL for 16 hours at 37° C.) or naloxone (10 µM for 30 minutes at 37° C.) or ODQ (10 µM for 30 minutes at 37° C.).

The results are shown in FIGS. 6A-C, 7 and 8.

Compound 1 did not appear to inhibit forskolin-stimulated cAMP formation in HEK293 cells transfected with δ-opioid receptors (DOP receptors) (FIG. 6A) or κ-opioid receptors (KOP receptors) (FIG. 6B) or in non-transfected HEK293 cells (FIG. 6C) across the entire concentration range tested. The standard compounds used were [D-Pen$^{2,5}$]-Enkephalin hydrate (DPDPE, DOP transfected cells), N-methyl-2-phenyl-N-[(5R,7S,8S)-7-pyrrolidin-1-yl-1-oxaspiro[4,5]dec-8-yl]acetamide (U69,593, KOP transfected cells) and morphine (non-transfected cells) as agonists at DOP, KOP and MOP receptors respectively.

Figure 7:
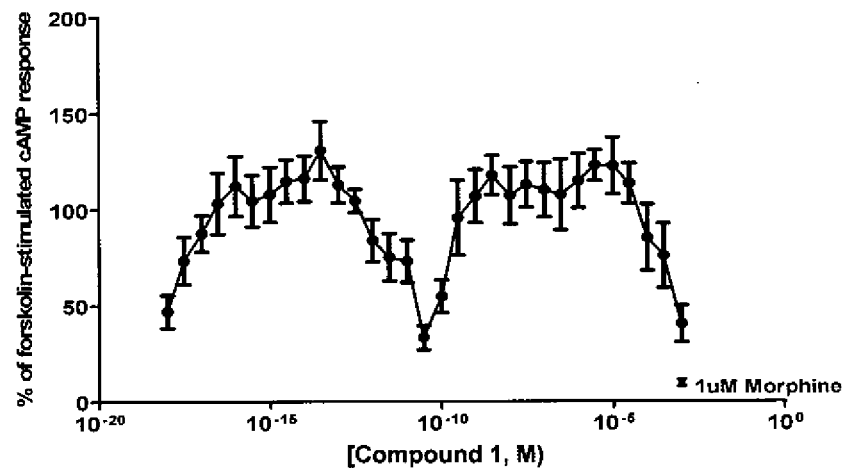
FIG. 7 provides a graphical representation showing the effects of Compound 1 on forskolin-stimulated cAMP responses in mu-opioid receptor (MOP)-transfected HEK293 cells (Data are means±SEM., n=8).

However, Compound 1 inhibited forskolin-stimulated cAMP formation in HEK293 cells transfected with µ-opioid receptors (MOP receptors) at mM, pM and aM concentrations in an analogous manner to morphine (FIG. 7).

Figure 8:
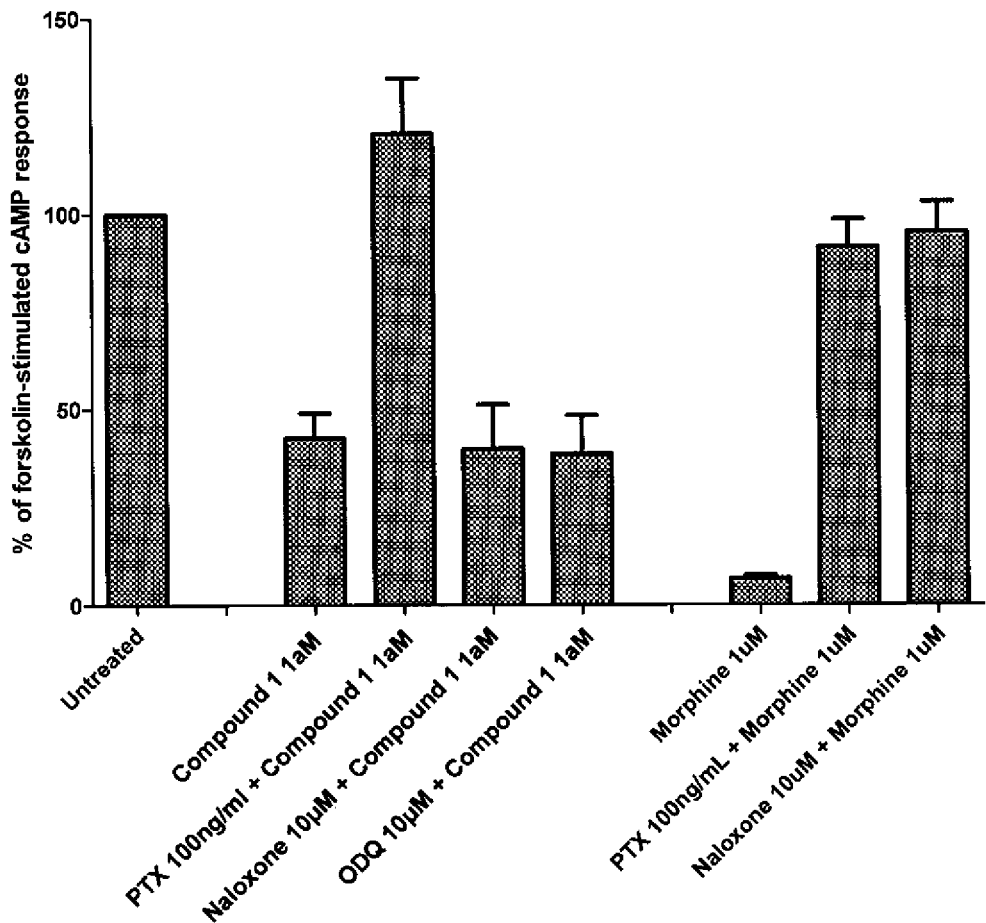
FIG. 8 provides a graphical representation showing the effects of pertussis toxin, naloxone or ODQ pretreatment on the forskolin-stimulated cAMP responses evoked by Compound 1 in MOP-transfected HEK293 cells (Data are means±SEM., n=4). **p<0.01 vs Compound 1 or morphine alone as determined by one-way ANOVA followed by Tukey's test.

The inhibition of forskolin-stimulated cAMP formation in MOP-transfected HEK293 cells produced by 1 aM of Compound 1 was abolished by pre-incubation with pertussis toxin but not by naloxone. In contrast, the inhibition of forskolin-stimulated cAMP formation in MOP-transfected HEK293 cells by 1 µM morphine was blocked by pre-incubation with both pertussis toxin and naloxone (FIG. 8).

Figure 9:
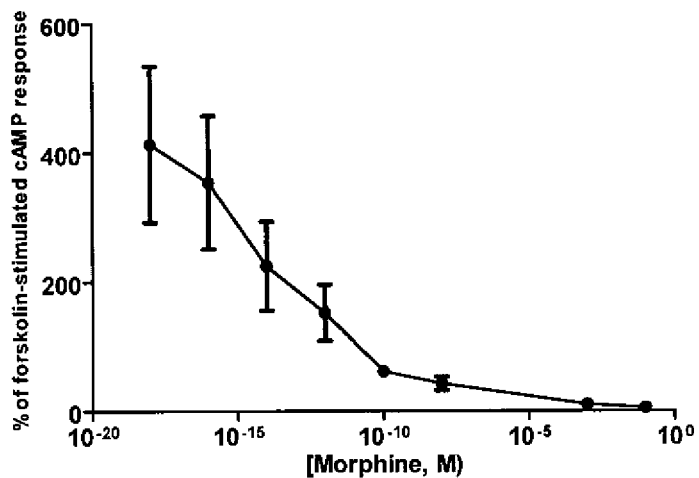
FIG. 9 is a graphical representation showing that morphine at pM-μM concentrations inhibited forskolin-stimulated cAMP formation in MOP-transfected HEK-293 cells whereas even lower concentrations of morphine produced stimulating responses. Data are presented as mean±SEM (n=3).

It was found that pM-µM concentrations of morphine inhibited forskolin-stimulated cAMP formation in a concentration-dependent manner with even lower concentrations of morphine producing superactivation of cAMP responses (FIG. 9).

Example 6

Displacement of Specific Binding of [$^3$H]-DAMGO from Membranes of MOP-Transfected HEK293 Cells A binding assay was performed to determine whether Compound 1 binds at the MOP receptor.

Stably transfected MOP-HEK cells were plated in a 3×10 cm dish and washed with (3×5 mL) 50 mM Tris-HCl (pH 7.4) when sufficiently confluent. The cells were scraped off the dish in 1.5 mL 50 mM Tris-HCl (pH 7.4) using a transfer pipette and place in 15 mL falcon tubes. The cells were sonicated for a 5 second burst and placed on ice. The protein concentration was estimated. The cells were transferred to a 1.5 mL eppendorf tube and centrifuged at 18,000 rcf for 30 minutes at 4° C. The supernatant was removed and the cells resuspended in 50 mM Tris-HCl (pH 7.4) and 1 mg/mL BSA. An aliquot containing 30-50 µg/200 µL protein was taken and [$^3$H]DAMGO was added (200 µL in Tris-HCl, pH 7.4) with varying concentrations of unlabelled [D-Ala$^2$, N-Me-Phe$^4$, Gly$^5$-ol]-enkephalin acetate (DAMGO) or Compound 1 (200 µL in Tris-HCl, pH 7.4), total volume 600 µL. The solution was incubated for 1 hour at room temperature with slow rotation.

Figure 10:
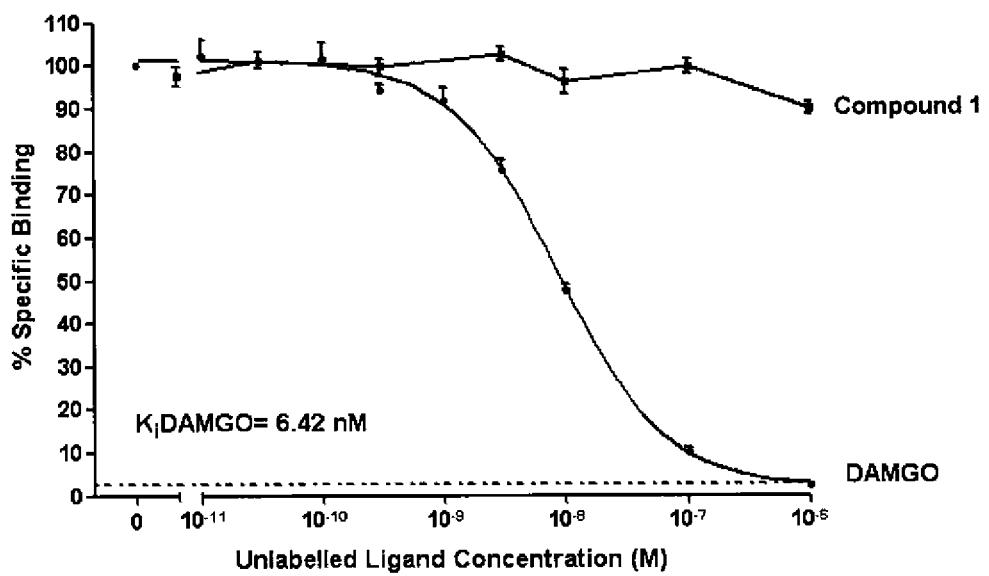
FIG. 10 provides a graphical representation showing the displacement of specific binding of [$^3$H]-DAMGO by unlabelled DAMGO and Compound 1 in membranes from MOP-transfected HEK293 cells (Data are means±SEM., n=8).

The results are shown in FIG. 10 and show that Compound 1 does not bind significantly to MOP receptors.

Example 7

Effects of Compound 1 on cGMP Production

For assessment of cGMP levels in MOP-transfected HEK cells, the methods used were similar to those described in Example 6 with the exception that forskolin was omitted from the incubations. cGMP levels were quantified using AlphaScreen detection kits according to the manufacturer's instructions. Briefly, 5 µL aliquots of the cell suspension were added to individual wells containing 5 µL aliquots of test or control article solutions at the concentration of interest in triplicates in 384-well plates and incubated for 30 min at 37° C. cGMP standard solutions were serially diluted in stimulation buffer to give concentrations in the range of $5 \times 10^{-10}$-$5 \times 10^{-6}$ M and were added at 10 µL/well. After cells were lysed with lysis buffer, 5 µL aliquots of acceptor bead mix (10 µl/mL of acceptor beads and 1/3000 anti-cGMP antibody for cGMP detection in lysis buffer) were added to each well. After plates were incubated in the dark at room temperature for 60 min, 5 µL aliquots of donor bead mix (10 µL/mL of donor beads and 0.3 nM biotinylated cGMP in lysis buffer) were added per well and plates were incubated for 16 h in the dark at room temperature. Bioluminescence was measured using an Envision Multilabel Plate Reader (PerkinElmer Life Sciences).

Figure 11:
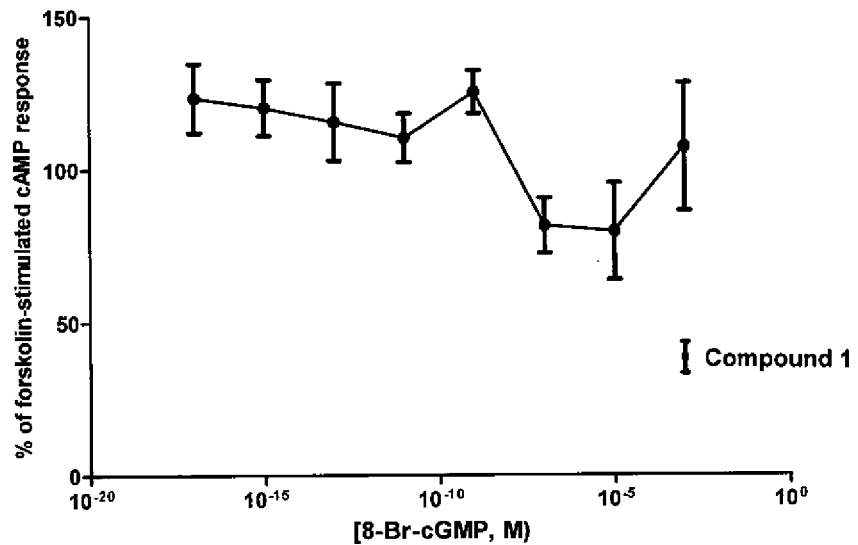
FIG. 11 is a graphical representation showing that the lack of effects of 8-Br-cGMP on forskolin-stimulated cAMP responses in MOP-transfected HEK293 cells.

Lack of Involvement of Guanylyl Cyclase in Effects of Compound 1 on Cellular cAMP Responses Pre-incubation of HEK-MOP cells with the sGC inhibitor, ODQ (10 µM), did not significantly attenuate the modulatory effects of Compound 1 on forskolin-stimulated cAMP formation (FIG. 8). As the cell membrane permeable cGMP analogue 8-Br-cGMP (FIG. 11, 8-Br-cGMP) did not inhibit forskolin-stimulated cAMP responses, the contribution of NO/sGC/cGMP signalling to the modulatory effects of Compound 1 on forskolin-stimulated cAMP formation, is further discounted.

Example 8

Role of Lipid Rafts/Caveolae in Modulation of Cellular cAMP Responses with Compound 1

Materials and Methods

Compound 1 was synthesised by Dr Craig Williams, School of Chemistry and Molecular Biosciences, The University of Queensland, Brisbane, Australia. (2-Hydroxypropyl)-β-cyclodextrin (βCD) and cholesterol (water soluble) were purchased from Sigma-Aldrich Pty Ltd (Sydney, Australia). Dulbecco's Modified Eagle Medium (DMEM) was purchased from Invitrogen (Mount Waverley, Australia).

As many signaling proteins including receptors, G-proteins, ion channels and effectors such as adenylyl cyclase, co-localize within lipid raft/caveolin-rich microdomains in the cell membrane to facilitate rapid signal transduction cross-talk between molecules (Ostrom Bundy, et al., *J. Biol. Chem.*, 2004, 279(19): 19846-19853), the role of caveolin in the effects of Compound 1 on forskolin-stimulated cAMP responses in HEK-MOP cells, was assessed. Briefly, HEK-MOP cells were pre-incubated with 2% (2-hydroxypropyl)-β-cyclodextrin (βCD) for 1 h at 37° C. to deplete cholesterol from caveolae in the cell membrane. Cells were washed with DMEM and then utilized in the forskolin-stimulated cAMP assay as described above. Following pre-incubation with 2% βCD for 1 h at 37° C. followed by washing with DMEM, additional βCD-treated HEK-MOP cells were then treated with βCD-cholesterol complexes (10 µg/mL cholesterol-βCD in a 1:6 molar ratio) to replenish cholesterol in caveolae in the cell membrane (Ostrom, Bundey et al. 2004, J. Biol. Chem., 279(19): 19846-19853). Cells were washed with DMEM and then utilized in the forskolin-stimulated cAMP assay as described above.

Figure 12:
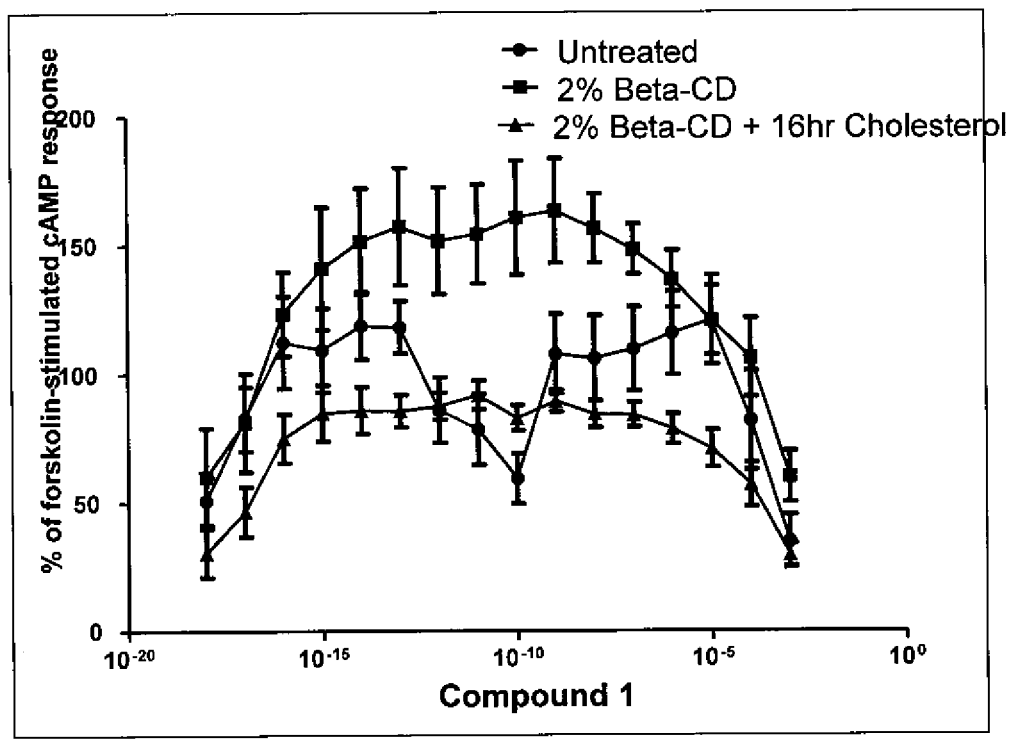
FIG. 12 is a graphical representation showing that the inhibitory effects of Compound 1 on forskolin-stimulated cAMP formation in MOP-transfected HEK293 cells are sensitive to removal of lipid rafts/caveolae from cell membranes.

Treatment of MOP-transfected HEK293 cells with 2% βCD to deplete lipid rafts/caveolae inhibited the effects of Compound 1 on forskolin-stimulated cAMP responses (FIG. 12), which were reversed upon delivering cholesterol back to the cells with βCD-cholesterol complexes (FIG. 12). These results are consistent with the notion that Compound 1 may act, at least in part, via modulation of transduction molecules residing in lipid rafts or caveolae domains to regulate downstream cAMP activity.

Example 9

In Vitro NO Release Profile of Compound 1

The extent of release of NO by the NO donor, Compound 1, was determined by measuring the concentration of the stable NO metabolite nitrite, ($NO_2^-$), using a modified Griess reagent assay involving the measurement of nitrite after conversion of nitrate to nitrite to give total $NO_x$ concentrations in samples. (Miranda, Espey et al. 2001, Nitric Oxide Biology and Chemistry, 5(1):62-71).

Briefly, HEK-MOP cells were seeded at $1 \times 10^5$ cells/mL and grown in 10 cm plates to 90% confluence. Four hours prior to experimentation, cell medium was replaced with phenol red-free DMEM. Cells were treated with either Compound 1 (1 mM±5 mM L-cysteine) or SIN-1 (1 mM and 10 nM) in 6 mL of phenol red-free DMEM and 500 µL samples of the cell-supernatant were collected prior to addition of the NO donor of interest and at the following times post-treatment: 1, 2, 5, 10, 20, 30, 45, 60, 120, 180 and 360 min. Following removal of each supernatant sample, it was replaced with 500 µL of phenol red-free DMEM. Samples were immediately placed on ice until $NO_x$ concentrations were quantified.

Sample aliquots (100 µL) were added to 96-well plates in duplicates. Nitrate was first converted to nitrite to determine total $NO_x$ concentrations with the addition of 100 µL aliquots of vanadium (III) chloride in 1M HCl (800 mg/100 mL) per well, followed by 100 µL aliquots of modified Griess reagent which converted nitrite to a deep purple azo derivative for spectrophotometric quantification at 560 nm using an Envision Multilabel Plate Reader (PerkinElmer Life Sciences). A standard curve was prepared in a similar manner to that used for the known concentrations of nitrite (3.125-200 µM) and the line of best fit was determined using linear regression as implemented in the GraphPad Prism™ 5.0 software program (GraphPad Software). Total $NO_x$ and nitrite concentration was determined through inverse prediction against the nitrite standard curve.

Over a 6-h study period in vitro, the mean (±SEM) amount of NO (as nitrate/nitrite) released by Compound 1 was 1.8% (±2.7) (Table 2). In a manner similar to other NO donors of the furoxan class, co-incubation of Compound 1 with L-cysteine (50 mM), increased $NO_x$ formation by 1.5-fold (from 1.8±0.3% to 2.7±0.3%, mean±SEM), likely due to an increase in thiol-dependent NO release.

TABLE 2

In vitro effects of the NO donor, Compound 1 (in the presence and absence of L-cysteine) on cGMP activity and extent of NO release (as Total NOx) over a 6-h study period.

| Compound | cGMP Activity (% of basal cGMP response) | Release of NO (Total NOx %) |
|---|---|---|
| Compound 1, 1 mM | 159 + 20 | 1.8 + 0.3 |
| Compound 1, 1 mM + ODQ, 10 μM | 114 + 17 | N/A |
| Compound 1, 1 mM + L-Cysteine 5 mM | 185 + 34 (1.2 fold increase) | 2.7 + 0.3 (1.5 fold increase) |

In HEK-MOP cells, Compound 1 in both the presence and absence of L-cysteine (5 mM), produced comparatively weak stimulation of cGMP formation in HEK-MOP cells. This finding suggests that the extent to which Compound 1 stimulates cGMP formation in HEK-MOP cells is correlated with the extent to which it releases NO.

Example 10

Figure 13:
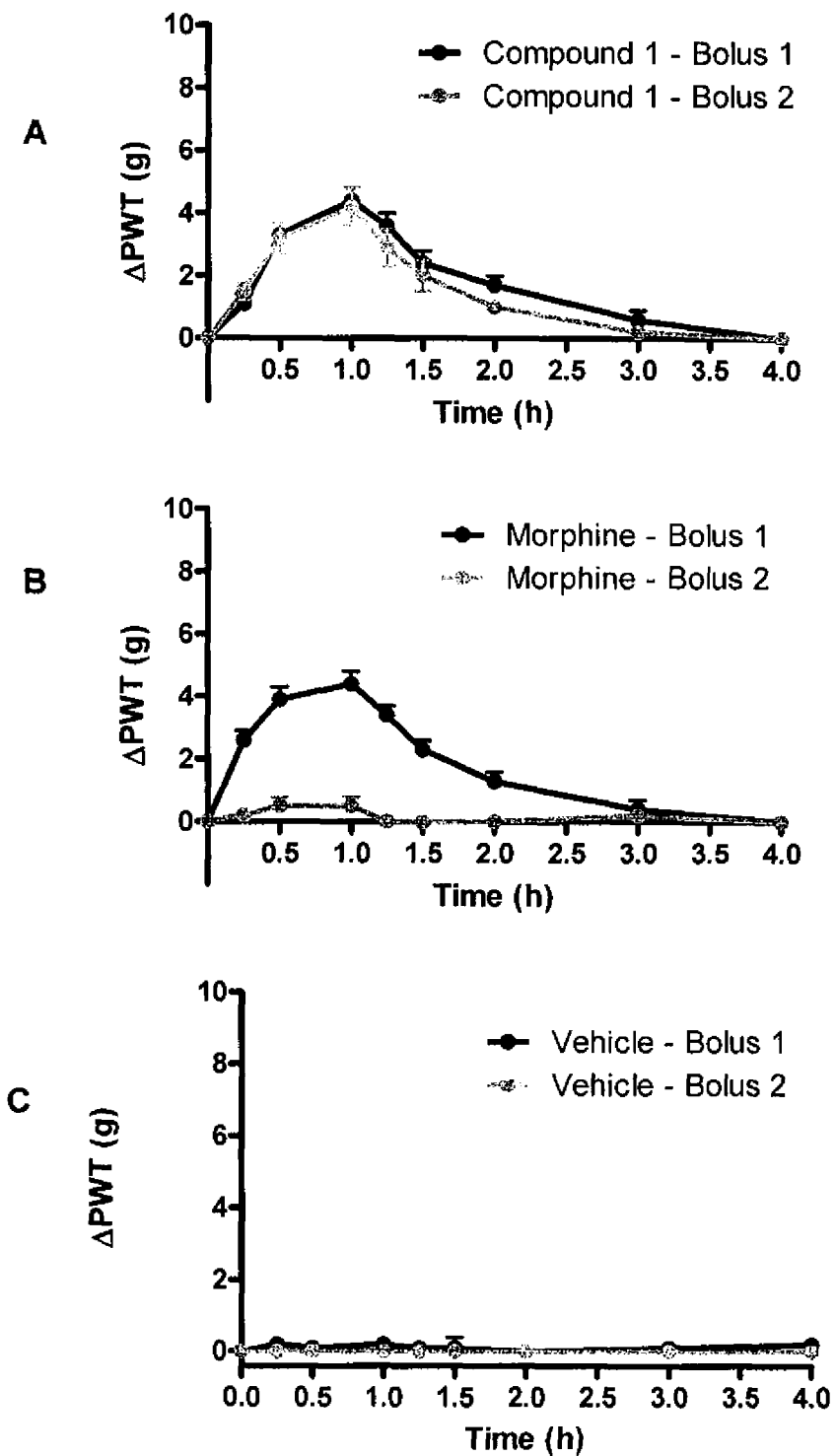
FIG. 13 is a graphical representation showing mean (±SEM) ΔPWT versus time curves following administration of single s.c. bolus doses of (A) Compound 1 (8 fmol/Kg), (B)

Comparison of the Development of Tolerance to Morphine and Compound 1 Induced Antinociception in Non-Diabetic Control Rats and in STZ-Diabetic Rats For drug-naïve non-diabetic control rats, there was a rapid onset of antinociception produced by single s.c. bolus doses of Compound 1 at 8 fmol/kg (FIG. 13A). Mean (±SEM) peak levels of antinociception occurred at 1 hour post-dosing [PWT: 15.9±0.3 g; ΔPWT: 4.4±(0.4) g] and the corresponding mean duration of action was ~3 hours. After completion of the 7-day continuous s.c. infusion of Compound 1 rats were completely tolerant to the antinociceptive effects of Compound 1. After a 2-day washout period, rats received a second s.c. bolus dose of Compound 1 at 8 fmol/kg. Following s.c. administration of the $2^{nd}$ single s.c. bolus dose of Compound 1, there was a consistent rapid onset of antinociception and the corresponding mean (±SEM) peak levels of antinociception appeared to occur 1 hour post-dosing [PWT: 15.6 (±0.7) g; ΔPWT: 4.2 (±0.6) g] with a corresponding mean duration of action of ~3 hours. It is clear from visual inspection of FIG. 13A, that the extent and duration of antinociception produced by single s.c. bolus doses of Compound 1 at 8 fmol/kg did not differ significantly (P>0.05) between that determined in drug naïve and "tolerant" rats.

For drug-naïve non-diabetic control rats administered single s.c. bolus doses of morphine (2.8 mmol/kg), there was a rapid onset of action with mean (±SEM) peak levels of antinociception observed at 1 hour post-dosing [PWT: 16.0 (±0.4) g; Δ PWT: 4.4 (±0.4) g] and a mean duration of action of ~3 hours (FIG. 13B). Following continuous s.c. infusion of morphine for 7-days, antinociceptive tolerance developed such that mean (±SEM) hindpaw PWT values did not differ (P>0.05) from baseline pre-dosing mean (±SEM) PWT values by 7-days of the infusion (FIG. 13B). After a 2-day washout period, rats received a second s.c. bolus dose of morphine at 2.8 mmol/kg. The corresponding PWT and ΔPWT versus time curves show that these rats were tolerant to the antinociceptive effects of morphine (FIG. 13B; peak PWT: 12 (±0.3) g; ΔPWT: 0.5 (±0.3) g) as insignificant (P>0.05) antinociception was produced; [ΔPWT AUC: 0.0 (±0.2) g·h.]. Following administration of vehicle either by single s.c. bolus or by continuous s.c. infusion for 7-days to control non-diabetic rats, there was a complete absence of antinociception confirming that neither the vehicle nor the experimental procedures themselves produce significant antinociception.

Following administration of single s.c. bolus doses of Compound 1 at 800 pmol/kg to drug-naïve STZ-diabetic rats, there was a rapid onset of anti-allodynia (FIG. 14A). Mean (±SEM) peak levels of anti-allodynia were observed at 1 h post-dosing [PWT: 11.6 (±0.6) g] and the corresponding mean duration of action was ~4 h (FIG. 14A). After completion of a 7-day s.c. infusion, STZ-diabetic rats were completely tolerant to the anti-allodynic effects of Compound 1. After a 2-day washout period, STZ-diabetic rats were administered a second s.c. bolus dose of Compound 1 at 800 pmol/kg. Again, there was a rapid onset of action with mean (±SEM) peak anti-allodynia observed at ~1 h post-dosing and a corresponding mean duration of action ~2-3 h. Comparison of the ΔPWT versus time curves shows significant reversal of tolerance in the STZ-diabetic rat group (FIG. 14 A).

For opioid-naïve STZ-diabetic rats administered single s.c. bolus doses of morphine (10.4 lμmol/kg), there was a rapid onset of anti-allodynia (FIG. 14B). Mean (±SEM) peak levels of anti-allodynia were observed at 1 h post-dosing [PWT: 10.7 (±0.3) g]; the corresponding mean duration of action was ~4 h. Following the continuous s.c. infusion of morphine, antinociceptive tolerance developed such that PWT values did not differ from baseline pre-dosing PWT values by 7-days of the s.c. infusion. After a 2-day washout, rats received a second s.c. bolus dose of morphine at 10.5 μmol/kg. The corresponding ΔPWT versus time curves show that these rats were tolerant to the anti-allodynic effects of morphine as insignificant anti-allodynia was produced in the hindpaws [FIG. 14B; mean (±SEM) peak PWT: 6.1±(0.5) g, mean (±SEM) peak ΔPWT: 1.0±(0.5) g]. Following administration of vehicle either by single s.c. bolus or by continuous s.c. infusion for 7-days to STZ-diabetic rats, there was a complete absence of anti-allodynia, confirming that neither the vehicle nor the experimental procedures themselves produce significant anti-allodynia in the hindpaws (FIG. 14C).

Example 11

Synthesis of Furoxan Compounds

Products were purified by column chromatography, preparative thin layer chromatography, filtration of a solid or recrystallisation.

General Synthetic Method A

The appropriate alpha, beta unsaturated aldehyde was treated with saturated sodium nitrite solution in glacial acetic acid to furnish the desired aldehyde substituted furoxan. Where appropriate, this intermediate represented a target structure.

The aldehyde was dissolved in 12 M $H_2SO_4$ solution and oxidized with aqueous potassium permanganate solution (0.83 eq.) overnight at room temperature to produce the acid product which represented an additional target molecule.

The acid was converted to the corresponding acid chloride with thionyl chloride in dichloromethane at reflux with catalytic DMF. The resulting acid chloride was treated with ammonia to produce the amide product.

General Synthetic Method B

The appropriate diketone starting material was treated with hydroxylamine hydrochloride in ethanol/water at reflux to furnish a 1,2-dioxime. This dioxime was oxidized to the desired furoxan ring structure via the use of either sodium hypochlorite in the presence of sodium hydroxide in ethanol at 5° C., or oxidised with chlorine in ethanol at room temperature.

In some cases, the diketone starting material was obtained by the oxidation of an appropriate phenylacetic acid by PCC/pyridine in dichloromethane at reflux.

General Synthetic Method C

The appropriate aldehyde or ketone starting material was treated with sodium borohydride in methanol at room temperature to provide an allylic alcohol. This alcohol was dissolved in glacial acetic acid and treated with aqueous sodium nitrite to provide the furoxan ring structure. Where appropriate, this represented a target structure.

The hydroxyl furoxan was oxidised to the aldehyde or ketone via the use of activated manganese dioxide in dichloromethane. This represented a target structure.

The aldehyde containing structures could be further oxidised with Jones reagent to provide access to the carboxylic acids. These represented further target structures.

The carboxylic acid intermediates could be further converted into amides by treatment with thionyl chloride in DCM at reflux with catalytic DMF to provide the intermediate acid chloride. The acid chloride was treated with ammonia in THF to provide the desired amide targets.

General Synthetic Method D

The appropriate 2-aminonitrobenezene was treated with sodium hypochlorite in the presence of methanol and potassium hydroxide in temperatures ranging from 5° C. to 120° C. This provided the target furoxan.

In a slight variation, the 2-aminonitropyridine was treated with iodosobenzene diacetate to produce the desired furoxan ring.

General Synthetic Method E 1,2-diphenyl-1,2,ethanedione or its di-4-fluorophenyl equivalent was treated with hydroxylamine hydrochloride at 70° C. to generate the mono oxime. This intermediate was further treated with hydroxylamine hydrochloride in the presence of sodium hydroxide at room temperature to generate the dioxime. The dioxime was treated with chlorine to produce the diaryl substituted furoxan target.

General Synthetic Method F 1,3-Cyclopentadione was reacted with sodium nitrite and then with hydroxylamine hydrochloride to generate the 1,2,3-trioxime. This intermediate was treated with sodium hypobromide to create the furoxan ring structure. The residual oxime functionality was converted back to a ketone via treatment with sulphuric acid and formaldehyde to furnish the desired ketofuroxan.

General Synthetic Method G

Cyclohexanone was treated with ethylnitrite in the presence of sodium nitrite and acetic acid to generate cyclohex-1,3-dioxime-2-one. Treatment of this with hydroxylamine hydrochloride in methanol provide the trioxime that was then oxidised to the furoxan ring with sodium hypobromide. The residual oxime was converted back to a ketone functionality via treatment with sulphuric acid and formaldehyde.

General Synthetic Method H

The appropriate aromatic aldehyde was treated with (ethyl) triphenylphosphonium iodide to generate the styrene intermediate. Due to its volatility, this alkene was converted directly without isolation to the furoxan ring structure via treatment with aqueous sodium nitrite in glacial acetic acid.

General Synthetic Method I

Aniline was treated with trifluoroacetic acid, triphenylphosphine and triethylamine in carbon tetrachloride to generate phenyl-(trifluoromethyliminochloride). This intermediate was treated with diethyl methylphosphonate and butyl lithium at low temperature followed by benzaldehyde. This provided the trifluoromethyl cinnamyl ketone. This material was then treated according to General Procedure C with the exception that the final oxidation was carried out with sodium hypochlorite in dichloromethane (instead of using activated manganese dioxide). This provided the furoxan target substituted with phenyl and trifluoromethyl ketone groups.

Table 3 identifies the compounds prepared by each route and provides mass spectral data.

TABLE 3

| Compound | Synthetic Method | Mass spectral data |
|---|---|---|
| 1 | A | 151 (MNa$^+$), 161 (MHCH$_3$OH$^+$) |
| 2 | B | 141.1 (MH$^+$), 163 (MNa$^+$) |
| 3 | D | 137 (MH$^+$), 159 (MNa$^+$) |
| 4 | D | 138 (MH$^+$), 160 (MNa$^+$) |
| 5 | E | 239 (MH$^+$), 261 (MNa$^+$) |
| 6 | A | No ions, $^1$H nmr shows singlet at 2.30 ppm |
| 7 | A | 144 (MH$^+$), 166 (MNa$^+$) |
| 8 | A | 159 (MH$^+$), 181 (MNa$^+$) |
| 9 | A | 158 (MH$^+$), 180 (MNa$^+$) |
| 10 | A | 173 (MH$^+$), 195 (MNa$^+$) |
| 11 | A | 172 (MH$^+$), 194 (MNa$^+$) |
| 12 | A | 143 (MH$^+$), 175 (MHCH$_3$OH$^+$), 197 (MCH$_3$OHNa$^+$) |
| 13 | B | 177 (MH$^+$), 199 (MNa$^+$) |
| 14 | C | 213 (MNa$^+$), 245 (MCH$_3$OHNa$^+$) |
| 15 | C | 275 (MCH$_3$OHNa$^+$) |
| 16 | F | No ions, $^1$H NMR shows multiplet centred on 3.36 ppm |
| 17 | G | 155 (MH$^+$), 177 (MNa$^+$) |
| 18 | C | No ions. $^1$H NMR shows 7.34 (d, 2H), 7.80 (d, 2H), 13.35 (s, 1H) |
| 19 | D | 157 (MH+), 179 (MNa+) (2 amu above theoretical mass) |
| 20 | D | 167 (MH$^+$), 189 (MNa$^+$) |
| 21 | E | 297 (MNa$^+$) |
| 22 | I | No ion. $^1$H NMR shows 7.61 (m, 3H), 7.90 (m, 2H) |
| 23 | H | 195 (MH$^+$), 217 (MNa$^+$), 248.9 (MCH$_3$OHNa$^+$) |
| 24 | B | 207 (MH$^+$), 229 (MNa$^+$), 261 (MCH$_3$OHNa$^+$) |
| 25 | C | 161.1 (M - CO$_2$H$^+$) |
| 26 | C | 206 (MH$^+$), 228 (MNa$^+$) |
| 27 | C | 205 (MH$^+$), 227 (MNa$^+$) |
| 28 | C | 263 (MCH$_3$OHNa$^+$) |
| 29 | C | 224 (MH$^+$), 245.9 (MNa$^+$) |
| 30 | C | 236 (MH$^+$), 258 (MNa$^+$) |
| 31 | C | 193 (MH$^+$), 215 (MNa$^+$) |
| 32 | C | 223 (MH$^+$), 245 (MNa$^+$) |

Example 12

Synthesis of Compound 33

Compound 33, 5-nitratopentanoic acid, was prepared using the method set out in EP0984012. Briefly, silver nitrate (23.48 g, 0.153 mol) was pre-dried under high vacuum (0.01 mmHg) and subsequently dissolved in anhydrous acetonitrile (70 mL) under an argon atmosphere. The solution was warmed to 50° C. and 5-bromovaleric acid (5 g, 0.028 mol), dissolved in 3 mL of anhydrous acetonitrile, was added quickly by syringe. A precipitate formed instantaneously. The mixture was then heated at 80° C. for 20 minutes. On cooling, the precipitate (AgBr) was removed by filtration. The filtrate was concentrated and the residue partitioned between ethyl acetate and water. The ethyl acetate layer was washed with water, dried (NaSO$_4$), concentrated and further dried under vacuum (0.01 mmHg). $^1$H NMR (300 MHz, CDCl$_3$) δ 1.68 (m, 4H), 2.41 (t, J=7.0 Hz, 2H), 4.45 (t, J=4.45 Hz, 2H). $^{13}$C NMR (75 MHz, CDCl$_3$) δ 20.8, 26.1, 33.2, 72.6, 179.3.

Example 13

Effects of Furoxan NO Donors, Compounds 1-32 on Forskolin-Stimulated cAMP Responses in HEK-293 Cells Transfected with μ-Opioid Receptors The assay described in Example 5 was repeated with Compounds 1-32 to assess the effects of the furoxan NO donors on forskolin-stimulated cyclic AMP responses in HEK-293 cells transfected with μ-opioid (MOP) receptors. The results are shown in Table 4 expressed as a % of forskolin stimulated cyclic AMP response. In a similar manner to compound 1 (FIG. 7), these compounds generally produced biphasic effects on forskolin-stimulated cAMP formation in HEK-293 cells transfected with MOP receptors.

forskolin-stimulated cyclic AMP response. This compound produced dose dependent inhibition of forskolin-stimulated cyclic AMP formation in HEK293 cells transfected with MOP receptors in the μm to mm range.

Example 15

NO Release Profiles of No Donors in a 1 and 6 Hour Assay

The assay described in Example 9 was repeated with Compounds 1, 6, 16, 22, 28, 31 and 33 with NOx analysis at 1 hour and 6 hours. The results are shown in Table 5.

TABLE 4

| | Conc (M) | | | | | | | |
|---|---|---|---|---|---|---|---|---|
| Comp | $10^{-18}$ | $10^{-17}$ | $10^{-16}$ | $10^{-15}$ | $10^{-14}$ | $10^{-13}$ | $10^{-12}$ | $10^{-11}$ | $10^{-10}$ |
| 5 (n = 3) | 68.7 | 75.8 | 91.2 | 117.0 | 105.6 | 102.3 | 119.1 | 76.3 | 79.2 |
| 6 (n = 3) | 60.4 | 83.9 | 149.0 | 79.0$^a$ | 98.2 | 128.0 | 91.1 | 88.0 | 61.5 |
| 8 (n = 3) | 72.8 | 115.0 | 140.5 | 97.6 | 94.8 | 112.7 | 128.3 | 88.3 | 79.4 |
| 13 (n = 3) | 61.2 | 105.3 | 88.3$^a$ | 101.5 | 99.4$^a$ | 89.6 | 108.8 | 66.3 | 106.9 |
| 14 (n = 3) | 95.1 | 120.5 | 129.8 | 103.8 | 103.4$^a$ | 94.2 | 92.8 | 62.7 | 69.5 |
| 15 (n = 3) | 94.7 | 107.6 | 119.5 | 80.2 | 166.8$^a$ | 71.5 | 77.7 | 57.5 | 122.0 |
| 16 (n = 3) | 62.4$^a$ | 100.4 | 108.3 | 97.7 | 106.3 | 98.8 | 59.3 | 67.1 | 101.3 |
| 18 (n = 3) | 54.7$^a$ | 94.1 | 89.6 | 90.4 | 85.3 | 85.4 | 82.2 | 77.5 | 83.6 |
| 21 (n = 3) | 38.7 | 49.1 | 67.7 | 64.0 | 59.7 | 61.5 | 42.9 | 29.9 | 38.4 |
| 22 (n = 7) | 47.0 | 59.4$^b$ | 73.2 | 89.0 | 104.6 | 70.5 | 62.4 | 59.2 | 66.1 |
| 23 (n = 3) | 80.2 | 73.6 | 77.1 | 80.4 | 79.2 | 87.6 | 74.7 | 75.7 | 56.5 |
| 24 (n = 3) | 70.0 | 70.0 | 88.0 | 97.0$^a$ | 75.1 | 82.3 | 90.1 | 79.4 | 60.2 |
| 27 (n = 3) | 56.5 | 108.6$^a$ | 162.4 | 115.4 | 78.2 | 88.3$^a$ | 66.7$^a$ | 84.4 | 46.0 |
| 28 (n = 3) | 47.3 | 63.9 | 56.2 | 100.2 | 107.6$^a$ | 93.5 | 105.0 | 64.3 | 46.5 |
| 31 (n = 3) | 94.5 | 48.5$^a$ | 54.8 | 42.2$^a$ | 77.5$^a$ | 85.7 | 81.4 | 61.0 | 42.8$^a$ |

| | Conc (M) | | | | | | |
|---|---|---|---|---|---|---|---|
| Comp | $10^{-9}$ | $10^{-8}$ | $10^{-7}$ | $10^{-6}$ | $10^{-5}$ | $10^{-4}$ | $10^{-3}$ |
| 5 (n = 3) | 57.7 | 73.6 | 112.7 | 142.4 | 120.4 | 99.8 | 69.6 |
| 6 (n = 3) | 88.2 | 111.2 | 110.5 | 109.7 | 138.7 | 115.0 | 8.1 |
| 8 (n = 3) | 107.0 | 114.3 | 102.9 | 104.7 | 90.0 | 68.2 | 6.8 |
| 13 (n = 3) | 94.9 | 80.3 | 78.8 | 84.5$^a$ | 109.4$^a$ | 67.1 | 40.2 |
| 14 (n = 3) | 107.4 | 113.2$^a$ | 121.5 | 110.6$^a$ | 51.0$^a$ | 40.7$^a$ | 8.5 |
| 15 (n = 3) | 129.4 | 88.3 | 104.5 | 101.0 | 84.1 | 61.6 | 3.7 |
| 16 (n = 3) | 125.4 | 62.2 | 119.9 | 83.5 | 105.2 | 44.3 | 18.9 |
| 18 (n = 3) | 142.3$^a$ | 81.7 | 91.9 | 101.0 | 97.7 | 79.0 | 7.1 |
| 21 (n = 3) | 46.5 | 57.5 | 47.3 | 53.0 | 63.5 | 42.1 | 7.1 |
| 22 (n = 7) | 65.2 | 82.1 | 68.4 | 87.5 | 77.9 | 18.2 | 0.3 |
| 23 (n = 3) | 64.0 | 98.2 | 89.0 | 90.0 | 66.2 | 121.2 | 46.6 |
| 24 (n = 3) | 132.4 | 53.8$^a$ | 94.3 | 56.7 | 131.1$^a$ | 106.7$^a$ | 71.2 |
| 27 (n = 3) | 56.4 | 86.4 | 83.2 | 60.0 | 128.2 | 73.8$^a$ | 22.4 |
| 28 (n = 3) | 84.9 | 91.5 | 67.6$^a$ | 101.7 | 72.8$^a$ | 54.9 | 16.0 |
| 31 (n = 3) | 76.8$^a$ | 36.2$^a$ | 108.4 | 60.0$^a$ | 96.9$^a$ | 182.4$^a$ | 3.8 |

$^a$n = 2;
$^b$n = 6
Controls used: Stimulation buffer (n = 18): 0%; Stimulation buffer and forskolin solution (n = 18): 100% DAMGO (1 μM) (n = 18): 5.5%; Morphine (1 μM) (n = 18): 6.6%

Example 14

Effects of Compound 33 on Forskolin-Stimulated cAMP Responses in HEK-293 Cells Transfected with μ-Opioid Receptors The assay described in Example 5 was repeated with Compound 33. The results are shown in FIG. 15 expressed as a %

TABLE 5

| NOx release Profiles over 1 and 6 hours | | |
|---|---|---|
| Compound | 1 Hour Total NOx (μM) | 6 Hours Total NOx (μM) |
| none | 0.86 | 0.310 |
| vehicle | 0.42 | 0.53 |

TABLE 5-continued

| | NOx release Profiles over 1 and 6 hours | |
|---|---|---|
| Compound | 1 Hour Total NOx (µM) | 6 Hours Total NOx (µM) |
| 1 | 2.08 | 2.52 |
| 1 | 2.19 | 2.52 |
| 6 | 0.31 | 0.53 |
| 16 | 1.08 | 1.19 |
| 22 | 1.63 | 2.52 |
| 28 | 8.94 | 10.04 |
| 31 | 8.60 | 12.92 |
| 33 | 13.14 | 67.69 |

Example 16

Anti-Allodynic Efficacy and Potency of NO Donor Compound 33

In rats confirmed to be hyporesponsive to the anti-allodynic effects of single s.c. bolus doses of morphine at 2661 nmol/kg (FIG. 16A), single s.c. bolus doses of Compound 33 (80, 120, 800, 1200 nmol/kg; n=6-10 per dose) were administered and relief from mechanical allodynia assessed by analysing paw withdrawal thresholds as described in Example 1.

Figure 16B:
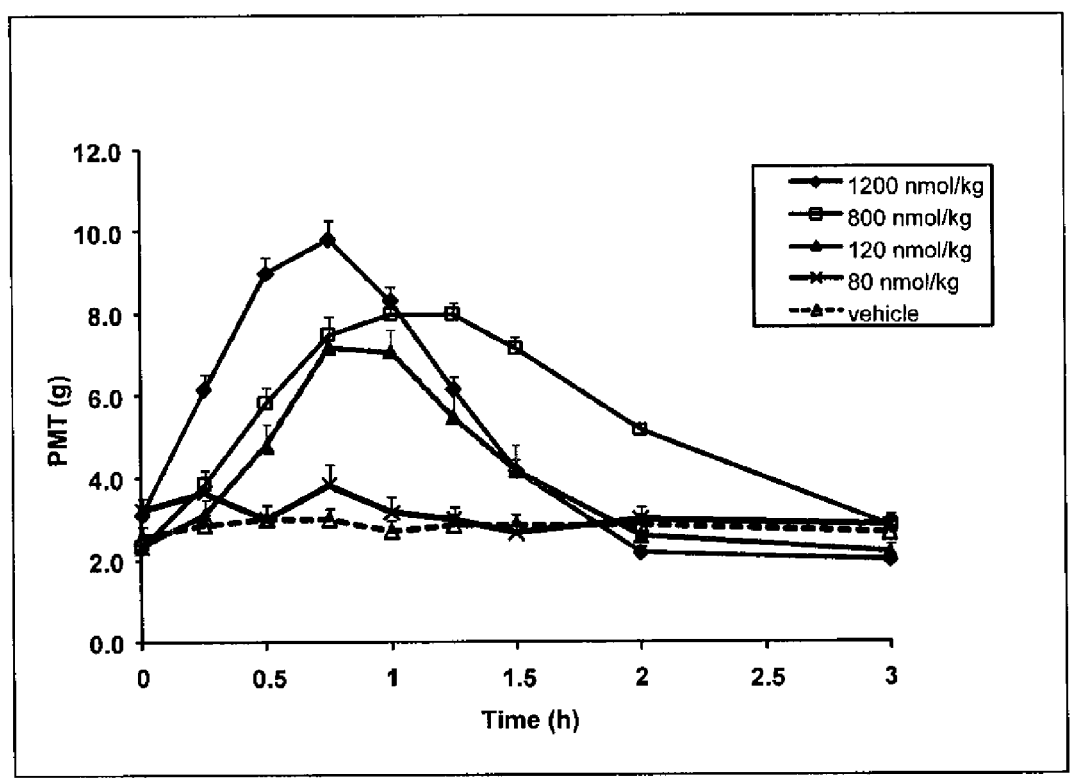

Compound 33 produced significant relief of mechanical allodynia at 120, 800 and 1200 nmol/kg. Peak levels of anti-allodynia were observed at about 0.75-1 hour post-dosing and the corresponding duration was 2-3 hours. In contrast, 80 nmol/kg of Compound 33 (n=6) produced insignificant relief, analogous to vehicle (n=7) as shown in FIG. 16B.

What is claimed is:

1. A method for treating neuropathic pain in a subject, the method consisting essentially of administering to the subject at least one NO donor at a level that enhances NO and that does not alter normal systemic vascular tone in the subject, wherein the at least one NO donor comprises a furoxan NO donor of formula (I):

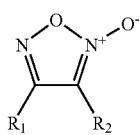

(I)

wherein $R_1$ and $R_2$ are independently selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylCO$_2$R$_3$, —$C_{0-6}$alkylC(O)R$_3$, —$C_{0-6}$alkylC(O)NHR$_4$, —$C_{0-6}$alkylN(R$_4$)$_2$, —$C_{0-6}$alkylN$^+$(R$_7$)$_3$, —$C_{0-6}$alkylOR$_5$, —$C_{0-6}$alkylSR$_5$, —$C_{0-6}$alkylC(=NR$_6$)R$_3$, —$C_{0-6}$alkylN=NR$_5$, —$C_{0-6}$alkylNR$_4$N(R$_4$)$_2$, —$C_{0-6}$alkylNR$_4$C(=NR$_4$)N(R$_4$)$_2$, —$C_{0-6}$alkylhalo, —$C_{0-6}$alkylS(O)R$_3$, —$C_{0-6}$alkylSO$_2$R$_3$, —CN and —NO$_2$; or $R_1$ and $R_2$ taken together form an optionally substituted 5 to 8 membered saturated or unsaturated carbocyclic or heterocyclic ring, an aryl ring or a heteroaryl ring;

$R_3$ is selected from hydrogen, alkyl, alkenyl, alkynyl, haloalkyl, 6alkylcycloalkyl, —$C_{0-6}$alkylcycloalkenyl, —$C_{0-6}$alkylaryl, —$C_{0-6}$alkylheterocyclyl, —$C_{0-6}$alkyl- heteroaryl, —$C_{1-6}$alkylCO$_2$R$_7$, —$C_{0-6}$alkylN(R$_4$)$_2$, —$C_{1-6}$alkylNR$_4$C(=NR$_4$)N(R$_4$,)$_2$ —$C_{1-6}$alkylOR$_7$ and —$C_{1-6}$alkylSR$_7$;

each $R_4$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylC(O)R$_8$, —$C_{0-6}$alkylC(S)R$_8$, —$C_{0-6}$alkylCO$_2$R$_7$, —$C_{0-6}$alkylSO$_2$R$_8$ and —$C_{0-6}$alkylOR$_7$;

$R_5$ is selected from hydrogen, alkyl, alkenyl, alkynyl, haloalkyl, 6alkylcycloalkyl, —$C_{0-6}$alkylcycloalkenyl, —$C_{0-6}$alkylaryl, —$C_{0-6}$alkylheterocyclyl, —$C_{0-6}$alkyl- heteroaryl, —$C_{0-6}$alkylC(O)R$_7$, —$C_{0-6}$alkylCO$_2$R$_8$, —$C_{0-6}$alkylN(R$_7$)$_2$, —$C_{0-6}$alkylC(O)N(R$_7$)$_2$, —$C_{0-6}$alkylNR$_4$C(=NR$_4$)N(R$_4$,)$_2$, —$C_{1-6}$alkylOR$_7$ and —$C_{1-6}$alkylSR$_7$;

$R_6$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl, —$C_{0-6}$alkylheteroaryl, —$C_{0-6}$alkylNHC(O)N(R$_7$)$_2$, —$C_{0-6}$alkylNHC(O)R$_7$, —$C_{0-6}$alkylNHSO$_2$R$_7$, —$C_{0-6}$alkylNHCO$_2$R$_7$, —$C_{0-6}$alkylOC(O)R$_7$, —$C_{0-6}$alkylC(O)R$_7$, —CN and —OR$_7$;

each $R_7$ is selected from hydrogen, alkyl, alkenyl, alkynyl, haloalkyl, —$C_{0-6}$alkylcycloalkyl, —$C_{0-6}$alkylcycloalkenyl, —$C_{0-6}$alkylaryl, —$C_{0-6}$alkylheterocyclyl and —$C_{0-6}$alkylheteroaryl; and $R_8$ is selected from hydrogen, alkyl, alkenyl, alkynyl, haloalkyl, 6alkylcycloalkyl, —$C_{0-6}$alkylcycloalkenyl, —$C_{0-6}$alkylaryl, —$C_{0-6}$alkylheterocyclyl, —$C_{0-6}$alkyl- heteroaryl and —N(R$_7$)$_2$;

wherein each alkyl, alkenyl, alkynyl, cycloalkyl, cycloalkenyl, aryl, heterocyclyl and heteroaryl group is optionally substituted; or a pharmaceutically compatible salt thereof; and wherein $R_1$ and $R_2$ are not both —$C_o$alkylN(R$_4$)$_2$.

2. A method according to claim 1, wherein the at least one NO donor is administered without co-administration of an opioid analgesic.

3. A method according to claim 1, wherein the level of NO is a sub-normovasodilatory (SNV) concentration that ranges from about ½ to about $10^{-15}$ of a reference concentration required to induce vasodilation in an anatomical site of a reference subject lacking a vascular condition.

4. A method according to claim 3, wherein the anatomical site is selected from kidney, skin, skeletal muscle, arm, leg, tail and gastro-intestinal tract.

5. A method according to claim 3, wherein the vascular condition associates with the neuropathic pain.

6. A method according to claim 5, wherein the neuropathic pain is associated with PDN.

7. A method according to claim 1, wherein the at least one NO donor is provided in a sustained release formulation.

8. A method according to claim 3, wherein an individual NO donor is a low-release NO donor that delivers the SNV concentration of NO to the subject.

9. A method according to claim 8, wherein the NO donor is administered as a bolus in the range of 0.000001 nmol/kg to 2 nmol/kg.

10. A method according to claim 8, wherein the NO donor is a transdermal patch adapted to release 0.5 nmol to 500 nmol of NO over at least 6 hours.

11. A method according to claim 1, wherein $R_1$ and $R_2$ are independently selected from —$C_{1-6}$alkyl, —$C_{3-8}$cycloalkyl, aryl, —C(O)aryl, —C(O)H, —C(O)alkyl, —C(O)haloalkyl, —NH$_2$, —NO$_2$, —Salkyl, —Saryl, —SO$_2$alkyl, —SO$_2$aryl, —CO$_2$H, —CO$_2$alkyl, —CO$_2$haloalkyl, —CO$_2$aryl, —NHC (O)alkyl, —NHC(O)aryl, —N═NH, —N═Nalkyl, —N═Naryl, —C(═NOH)H, —OH, —Oalkyl, —Oaryl, —OC(O)alkyl, —OC(O)aryl, —OC(O)NH$_2$, —OC(O)NH(alkyl), —OC(O)N(alkyl)$_2$, —OC(O)N(alkyl)(aryl), —OC(O)N(aryl)$_2$, —OC(O)NH(aryl), —CH═NNHCO$_2$alkyl, —CH═NNHCO$_2$aryl, —CH═NNHC(O)NH$_2$, —CH═NNHC(O)NH(alkyl), —CH═NNHC(O)N(alkyl)$_2$, —CH═NNHC(O)NH(aryl), —CH═NNHC(O)N(alkyl)(aryl), —CH═NNHC(O)N(aryl)$_2$, —CH═NNHSO$_2$alkyl, —CH═NNHSO$_2$aryl, —CN, —CH$_2$OH, —C(O)NH$_2$, —C(O)NH(alkyl), —C(O)N(alkyl)$_2$, —C(O)NH(aryl), —C(O)N(alkyl)(aryl), —C(O)N(aryl)$_2$, —OalkylNH$_2$, —OalkylNH(alkyl), —OalkylN(alkyl)$_2$, —OalkylNHaryl, —OalkylN(aryl)$_2$, —OalkylN(aryl)(alkyl), —SalkylNH$_2$, —S alkylNH(alkyl), —S alkylN(alkyl)$_2$, —S alkylNHaryl, —S alkylN(aryl)$_2$, —SalkylN(aryl)(alkyl), —CH$_2$NH$_2$, —CH$_2$NH(alkyl), —CH$_2$N(alkyl)$_2$, —CH$_2$NH(aryl), —CH$_2$N(alkyl)(aryl), —CH$_2$N(aryl)$_2$, —C(O)heterocyclyl, —C(O)heteroaryl, —C(O)heterocyclyl-heteroaryl, —C(O)heteroaryl-heterocyclyl, —C(O)heterocyclyl-heterocyclyl, —C(O)heteroaryl-heteroaryl, —OalkylNHalkylOaryl, —OalkylNHC(O)heteroaryl and —OalkylOC(O)aryl, wherein each alkyl, aryl, heterocyclyl and heteroaryl is optionally substituted, or where $R_1$ and $R_2$ taken together with the carbon atoms to which they are attached form an optionally substituted 5 or 6 membered carbocyclic, aryl, heterocyclic or heteroaryl ring.

12. A method according to claim 1, wherein $R_1$ and $R_2$ are independently selected from methyl, ethyl, propyl, isopropyl, cyclopentyl, cyclohexyl, phenyl, 4-fluorophenyl, 4-methoxyphenyl, 4-CH$_3$SO$_2$phenyl-, 4—NH$_2$SO$_2$phenyl-, 4-CH$_3$Sphenyl, phenylSO$_2$—, phenylS—, —NO$_2$, —NH$_2$, —C(O)H, —C(O)CH$_3$, —C(O)CF$_3$, —C(O)phenyl, —C(O)-4-fluorophenyl, —C(O)-4-chlorophenyl, —C(O)-2-chlorophenyl, —C(O)-2-methylphenyl, —C(O)-4-methylphenyl, —C(O)-2-methoxyphenyl, —C(O)-4-methoxyphenyl, —C(O)-4-cyanophenyl, —C(O)-3-cyanophenyl, —CO$_2$H, —NHC(O)CH$_3$, —N═N—H, —C(═NOH)H, —OH, —CH═NNHC(O)NHbutyl, —CH═NNHSO$_2$phenyl, —CH═NNHC(O)NHaryl, —CN, —OC(O)N(CH$_3$)(propyl), —CH$_2$OH, —C(O)NH$_2$, —OCH$_2$CH$_2$N(CH$_3$)$_2$, —SCH$_2$CH$_2$NH$_2$, —SCH$_2$CH$_2$N(CH$_3$)$_2$, —Omethyl, Oethyl, —CH$_2$N(CH$_3$)$_2$, —NHpropylOphenylCH$_2$—N-piperidine, —C(O)-1-piperidine-4-[2-(4-amino-6,7-dimethoxy-quinazoline)], —OpropylNH-(2-hydroxypropyl)oxynaphthalene, —Opropyl-NHC(O)-3-pyridine and O-alkylOC(O)-(2-acetylphenyl), or $R_1$ and $R_2$ taken together with the carbon atoms to which they are attached form a cyclopentyl ring, 2-oxo-cyclopentyl ring, cyclohexyl ring, 2-oxo-cyclohexyl ring, phenyl ring, 3-fluorophenyl ring, 3-methoxy-phenyl ring, 2N-pyridine ring or 3-N-pyridine ring.

13. A method according to claim 1 wherein $R_1$ and/or $R_2$ include a carbonyl or hydroxyl substituent or where $R_1$ and $R_2$ taken together form a 5-8 membered saturated or unsaturated carbocyclic or heterocyclic ring substituted with an oxo (═O) group.

14. A method according to claim 1 wherein $R_1$ and/or $R_2$ include an optionally substituted phenyl ring.

15. A method according to claim 1 wherein $R_1$ and $R_2$ include a carbonyl or hydroxyl substituent and the other includes an optionally substituted phenyl ring.

16. A method according to claim 1 wherein the furoxan NO donor is 4-formyl-3-methyl-1,2,5-oxadiazole-2-oxide (Compound I).

17. A method according to claim 1 wherein the furoxan NO donor is administered together with another treatment for neuropathic pain.

\* \* \* \* \*

UNITED STATES PATENT AND TRADEMARK OFFICE
CERTIFICATE OF CORRECTION

PATENT NO. : 8,822,509 B2
APPLICATION NO. : 12/494183
DATED : September 2, 2014
INVENTOR(S) : Maree Therese Smith It is certified that error appears in the above-identified patent and that said Letters Patent is hereby corrected as shown below:

On the Title Page,

In column 1 (page 2, item 56) at line 14, Under Other Publications, change "opoid" to --opioid--.

In the Specification,

In column 1 at line 61, Change "S1118-30 2006)." to --S118-30 2006).--.

In column 4 at line 31, Change "$N(R_4,)_2,$" to --$N(R_4)_2,$--.

In column 4 at line 31, Change "$N(R_4,)_2,$" to --$N(R_4)_2,$--.

In column 4 at line 41, Change "$N(R_4,)_2$" to --$N(R_4)_2,$--.

In column 4 at line 53, Change "$N(R_4,)_2,$" to --$N(R_4)_2,$--.

In column 7 at line 1, Change "(2.8 lμmol/Kg)" to --(2.8 μmol/Kg)--.

In column 9 at line 1, Change "cyclopropentyl," to --cyclopropenyl,--.

In column 13 at line 15, Change "Guillian-Barre" to --Guillain-Barre--.

In column 13 at line 31, Change "Guillian-Barre" to --Guillain-Barre--.

In column 14 at line 31, Change "$N(R_4,)_2,$" to --$N(R_4)_2,$--.

In column 14 at line 31, Change "$N(R_4,)_2,$" to --$N(R_4)_2,$--.

In column 14 at line 41, Change "$N(R_4,)_2$" to --$N(R_4)_2,$--.

In column 14 at line 53, Change "$N(R_4,)_2,$" to --$N(R_4)_2,$--.

In column 16 at line 8, Change "carboxyclic" to --carboxylic--.

In column 17 at line 16, Change "Pergammon" to --Pergamon--.

In column 17 at line 24, Change "Pergammon" to --Pergamon--.

In column 17 at line 38, Change "hypobromide" to --hypobromite--.

In column 21 at line 19, Change "memantin" to --memantine--.

In column 25 at line 13 (approx.), Change "memantin" to --memantine--.

Signed and Sealed this
Sixth Day of October, 2015

Michelle K. Lee
*Director of the United States Patent and Trademark Office*

CERTIFICATE OF CORRECTION (continued)
U.S. Pat. No. 8,822,509 B2

In column 26 at line 2, Change "12 h/2 h" to --12 h/12 h--.

In column 26 at lines 47-48, Change "xyalazine" to --xylazine--.

In column 29 at lines 31-32, Change "80lμmol/kg." to --80 μmol.kg.--.

In column 30 at line 19, Change "(53.4 μmol•kg s.c.)," to --(53.4 μmol/kg s.c.),--.

In column 35 at line 60, Change "caveloae" to --caveolae--.

In column 38 at line 21, Change "((10.4 lμmol/kg),)" to --(10.4 μmol/kg),--.

In column 39 at line 26, Change "2-aminonitrobenezene" to --2-aminonitrobenzene--.

In column 39 at lines 44-45, Change "hypobromide" to --hypobromite--.

In column 39 at line 54, Change "hypobromide." to --hypobromite.--.

In the Claims,

In column 43 at line 59, In Claim 1, change "N(R$_4$,)$_2$," to --N(R$_4$)$_2$,--.

In column 43 at line 66, In Claim 1, change "6alkylcycloalkyl," to -- -C$_{0-6}$alkylcycloalkyl,--.

In column 44 at line 2, In Claim 1, change "N(R$_4$,)$_2$" to --N(R$_4$)$_2$,--.

In column 44 at line 11, In Claim 1, change "6alkylcycloalkyl," to -- -C$_{0-6}$calkylcycloalkyl,--.

In column 44 at line 15, In Claim 1, change "N(R$_4$,)$_2$." to --N(R$_4$)$_2$,--.

In column 44 at line 29, In Claim 1, change "6alkylcycloalkyl," to -- -C$_{0-6}$alkylcycloalkyl,--.

In column 44 at line 36, In Claim 1, change "-C$_o$alkylN(R$_4$)$_2$." to -- -C$_{0-6}$alkylN(R$_4$)$_2$.--.

In column 45 at line 15, In Claim 11, change "--S alkylNH(alkyl)," to -- --SalkylNH(alkyl),--.

In column 45 at line 15, In Claim 11, change "--S alkylN(alkyl)$_2$," to -- --SalkylN(alkyl)$_2$,--.

In column 45 at line 15, In Claim 11, change "--S alkylNHaryl," to -- --SalkylNHaryl,--.

In column 45 at line 16, In Claim 11, change "--S alkylN(aryl)$_2$," to -- --SalkylN(aryl)$_2$,--.